(12) United States Patent
Gaudet et al.

(10) Patent No.: US 6,743,579 B1
(45) Date of Patent: Jun. 1, 2004

(54) GLYCEROL AS A PREDICTOR OF GLUCOSE TOLERANCE

(75) Inventors: Daniel Gaudet, Chicoutimi (CA); John D. Rioux, Cambridge, MA (US); Steve Arsenault, Quebec (CA); Thomas J. Hudson, Westmount (CA); Mark Daly, Arlington, MA (US)

(73) Assignees: Whitehead Institute for Biomedical Research, Cambridge, MA (US); Complexe Hospitalier de la Sagamie, Quebec (CA)

( * ) Notice: Subject to any disclaimer, the term of this patent is extended or adjusted under 35 U.S.C. 154(b) by 0 days.

(21) Appl. No.: 09/694,088

(22) Filed: Oct. 20, 2000

Related U.S. Application Data

(60) Provisional application No. 60/161,141, filed on Oct. 22, 1999.

(51) Int. Cl.[7] ............................................... C12Q 1/68
(52) U.S. Cl. .......................................................... 435/6
(58) Field of Search ............................................. 435/6

(56) References Cited

U.S. PATENT DOCUMENTS 4,636,465 A    1/1987   Itoh et al.

OTHER PUBLICATIONS

Mahairas, G. et al., "Sequence–Tagged Connectors: A Sequence Approach to Mapping and Scanning the Human Genome," *Proceedings of the National Academy of Sciences of the United States of America*, 96(17) :9739–9744.

Mahairas et al., HS_5333_B1_GO6_SP6E RPCI–11 Human Male BAC Library Homo sapiens genomic clone Plate+909 Col–11 Row=N, genomic survey sequence, EMBL Database [online], 1999 [retrieved on Apr. 25, 2001]. Retrieved from the Internet <URL:http://srs.ebi.ac.uk/srs6bin/cgi–bin/wgetz?–id+b9841Gitof+–e+ [EMBL: 'AQ673121']> Accession No. AQ673121.

Hagström–Toft, E. et al., "Lipolytic response during spontaneous hypoglycaemia in insulin–dependent diabetic subjects," *Hormone and Metabolic Research* 30(9) :586–593 (1998).

Sargent, C.A. et al., "Five cases of isolated glycerol kinase deficiency including two families: Failure to find genotype:phenotype correlation," *Journal of Medical Genetics* 37 (6) :434–441 (2000).

Sargent, C.A., Homo sapiens partial GK gene for glycerol kinase, exon 12 (glycerol kinase deficiency case), EMBL Database [Online], 1999 [retrieved on Apr. 25, 2001]. Retrieved from the Internet <URL:http://srs.ebi.ac.uk/srs6bin/cgi–bin/wgetz?–id+b9841Gitof+–e+ [EMBL: 'AQ673121']> Accession No. HSA252563/AJ252563.

Schoonderwoerd K. et al., "Enhanced Lipolysis of Myocardial Triglycerides During Low–flow Ischemia and Anoxia in the Isolated Rat Heart," *Basic Research in Cardiology* 84(2):165–173 (1989).

Uhal, B.D. and Longmore, W.J., "Altered Glycerol Metabolism in the Type II Pneumocyte Isolated from Stretozotocin–Diabetic and BB Wistar Spontaneously Diabetic Rats, " *Federation Proceedings* 44 (5) :1606 (1985). Abstract 6992.

Gaudet, et al., "Glycerol as a Correlate of Impaired Glucose Tolerance: Dissection of a Complex System by Use of a Simple Genetic Trait", *Am. J. Hum. Genet.* 66: 1558–1568 (2000).

Sargent, et al., "H. sapiens glycerol kinase gene deficiency locus", GenBank Accession No. X78211 (1994).

Pelkonen, et al., "Metabolism of Glycerol on Diabetes Mellitus", *Diabetologia* 3(1): 1–8 (1967).

Rose and Haines, "Familial Hyperglycerolemia", *J. Clin. Invest.* 61: 163–170 (1978).

Pettigrew, et al., "Conserved Active Site Aspartates and Domain–Domain Interactions in Regulatory Properties of the Sugar Kinase Superfamily", *Archives of Biochemistry and Biophysics* 349(2): 236–245 (1998).

Sjarif, et al., "Clinical heterogeneity and noverl mutations in the glycerol kinase gene in three families with isolated glycerol kinase deficiency", *J. Med. Genet.* 35(8) : 650–656 (1998).

Walker, et al., "Mutations and Phenotype in Isolated Glycerol Kinase Deficiency", *Am. J. Hum. Genet.* 58: 1205–1211 (1996).

Blomquist, et al., "Glycerol kinase deficiency in two brothers with and without clinical manifestations", *Clin. Genet.* 50: 375–379 (1996).

*Primary Examiner*—Patrick J. Nolan
(74) *Attorney, Agent, or Firm*—Ropes & Gray LLP

(57) ABSTRACT

Novel alterations in the glycerol kinase gene are described. Also described are methods of predicting or assisting in the prediction of impaired glucose tolerance and type 2 diabetes mellitus.

7 Claims, 17 Drawing Sheets

Figure 3A

N288D
[boxes numbered 1-18, with 9A, 9B highlighted near N288D arrow]

G TAT GGA ACA GGA TGT TTC CTA TGT ᴬ⁄G AT ACA GGC CAT AAG
                                     270                    310

Figure 3B

| | | |
|---|---|---|
| GK N288D Mutant | FQIGQAKNTYGTGCFLLQDYTGHKCVFSDHGLLTTVAYKLGR | SEQ ID NO: 6 |
| glpk_human | FQIGQAKNTYGTGCFLLQNTGHKCVFSDHGLLTTVAYKLGR | SEQ ID NO: 7 |
| glpk_rat | FQDGQAKNTYGTGCFLLQNTGHKCVFSEHGLLTTVAYKLGR | SEQ ID NO: 8 |
| glpk_mouse | FQDGQAKNTYGTGCFLLQNTGHKCVFSEHGLLTTVAYKLGR | SEQ ID NO: 9 |
| glpk_ecoli | VKEGMAKNTYGTGCFMLMNTGEKAVKSENGLLTTIAC--GP | SEQ ID NO: 10 |
| glpk_pseae | VEPGQAKNTYGTGCFLLNETGDKAVKSTHGLLTTIAC--GP | SEQ ID NO: 11 |
| glpk_entca | FEKGMIKNTYGTGAFIVMNTGEEPQLSDNDLLTTIGY--GI | SEQ ID NO: 12 |
| glpk_haein | VHAGQAKNTYGTGCFMLLETGNKAITSRNGLLTTIACNAKG | SEQ ID NO: 13 |
| glpk_bacsu | FEEGMGKNTYGTGCFMLMNTGEKAIKSEHGLLTTIAW--GI | SEQ ID NO: 14 |
| glpk_yeast | YKPGRAKCTYGTGCFLLYNTGTKKLISQHGALTTLAFWFPH | SEQ ID NO: 15 |
| glpk_mycge | TEPGMVKNTYGTGCFVLMNIGDXPTLSKHNLLTTVAWQLEN | SEQ ID NO: 16 |
| glpk_entfa | FEPGMVKNTYGTGSFIVMNTGEEPQLSKNNLLTTIGY--GI | SEQ ID NO: 17 |
| glpk_mycpn | VEPAMVKNTYGTGCFMLMMIGNELKYSQHNLLTTVAWQLEN | SEQ ID NO: 18 |
| glpk_syny3 | DRPGLLKCTYGTGAFLVANTGQTVTRSQHRLLSTVAMTQTN | SEQ ID NO: 19 | poly: A/G
location: 13th base of exon 3

ATGCCTTCTTTTGTCAAAGATGGGTGGAACA [A/G] GACCCTAAGGAAATTCTACAT
 TCTGTCT  SEQ ID NO: 1

CAA vs CAG ==> silent poly: A/C
location: 17th base of intron 8
 TAATGGTAAAAAACAAACAAA [A/C] AAACAAAAAACACACCAAAAAACCAA
   SEQ ID NO: 2 poly: A/G
location: 29th base of exon 10

TTCATTCTCCCTTCAACCATAGGTATGGAACAGGATGTTTCTTACTATGT [A/G] AT
 ACAGGCCATAAGGTtGGTTTTTAATAAAAATGATTAAGTCA  SEQ ID NO: 3

AAT vs GAT ==> N to D poly: G/T
location: 22nd base of intron 12
 GAAATTGGTGAGTGTGTTCTAACAAAAG [G/T] TTAGAAAATCTGAAAAATGACACA
 TTTCA  SEQ ID NO: 4

Figure 6

SEQ ID NO: 5

Exon 1:
GGTTCAGCGGACGCGCGCGGCCTCGGTCTCTGGACTCGTCACCTGCCCCTCCCCCTCCCGCC
GCCGTCACCCAGGAAACCGGCCGCAATCGCCGGCCGACCTGAAGCTGGTTTCATGGCAGCCT
CAAAGAAGGCAGTTTTGGGGCCATTGGTGGGGGCGGTGGACCAGGGCACCAGTTCGACGCGC
TTTTTGGTGAGCCCGGGGTGACATGTGAAGAGGCGCTGAGC Exon 2:
TGTAAAACGACGGCCAGTCATCCTTGATATCTGCCTGCATTTTTACATTAATATTACAATAT
CTTTTTCAGGTTTTCAATTCAAAAACAGCTGAACTACTTAGTCATCATCAAGTAGAAATAAA
ACAAGAGTTCCCAAGAGAAGGGTATGTTTCCTAATTTAATATGTAAAGACACATTATGTTTG
TTAGTCCATCTCACCCAACTTGCCC Exon 3:
CAATGCCTTCTTTTGTCAAAGATGGGTGGAACA[A/G]GACCCTAAGGAAATTCTACATTCT
GTCTATGAGTGTATAGAGAAAACATGTGAGAAACTTGGACAGCTCAATATTGATATTTCCAA
CATAAAAGGTATTTTAGTAGAATATTTTACCCACA Exon 4:
TGTAAAACGACGGCCAGTTGAGAGCTGTTTTCCTGAAGTAGTTCCTACTTGTTAAATTTTTG
ACTTCCTTCTGTTTAACTTTCTCTTTAAAGCTATTGGTGTCAGCAACCAGAGGGAAACCACT
GTAGTCTGGGACAAGATAACTGGAGAGCCTCTCTACAATGCTGTGGGTAAGCTGTCATGCAT
GGATGTCAAATGTAGGGCCTTTCTTCACATTGCAA Exon 5:
TGTAAAACGACGGCCAGTTCCTTGATAGTGATTTCAGTAAGTTCTTATTTTTTTAAATGAAG
TTTTTCATGTATATTATTTTATTTTGGTCTATAGTGTGGCTTGATCTAAGAACCCAGTCTAC
CGTTGAGAGTCTTAGTAAAAGAATTCCAGGAAATAATAACTTTGTCAAGGTAAGAATTTCTT
CAGAAGTATACTATAAGAATGTTTCTTTTTTAAAAAAAGTTTGCAGATTTCACTAGAAAGA
AGCATCTTATGGTACAATAGTTATTTGATACAATTTATAGAATCTTTTTCCCGGATAATTGA
GGCC Exon 6:
TGTAAAACGACGGCCAGTTTCTTTTGTTTGGTGGTTTTGTTTTAAACTGTTACACTTTTCAT
TTGCTAACTGAACTTCACAACTGCTTTTAGTCCAAGACAGGCCTTCCACTTAGCACTTACTT
CAGTGCAGTGAAACTTCGTTGGCTCCTTGACAATGTGAGAAAAGTTCAAAAGGCCGTTGAAG
AAAAACGAGCTCTTTTTGGGACTATTGATTCATGGCTTATTTGGGTATGTTTAAATATAATG
GATATATGGAGAATTTTTTCAGAAATTTTTTCTAGACTGCCTTGCCTATTGTTTCTACTAGC
AGGTCAGACTTTTTAATTAGCA

Figure 7A

Exon 7:
TGTAAAACGACGGCCAGTTGTGCTCTGCTGATTATGACCCTTAACAATATGTAAATTAAATT
GCCAATAAGTACAAATTTAACCTGATTTTTTTACTCTGCCTAGAGTTTGACAGGAGGAGTCA
ATGGAGGTGTCCACTGTACAGATGTAACAAATGCAAGTAGGACTATGCTTTTCAACATTCAT
TCTTTGGAATGGGATAAACAACTCTGCGAGTAAGTTCTGTTTGCTCTAAATATAGTTTTCC
CAATACACTACCTATTTATAACCGAATCTTAATATTTTCAGATGTCAGTGGAGCA Exon 8:
TGTAAAACGACGGCCAGTACAGTGTTAAATACCCAATCTTCTTGTTTTTCAGATTTTTTGGA
ATTCCAATGGAAATTCTTCCAAATGTCCGGAGTTCTTCTGAGATCTATGGCCTAATGGTAAA
AAACAAACAAA [A/C] AAACAAAAAACACACCAAAAAACCAAAAAACAAACAAAAAAAAACC
TAATAATTAAAGTTTTTTTATTACAAAACAAGTTTACTATTCATAATTCAAAAGTCAACTGT
GTTATGTTTGTGACTTAAAAACTTTACAGTCCTTTTTACAATGG Exons 9A and 9B
AAAGCTGGGGCCTTGGAAGGTGTGCCAATATCTGGGGTAAGTTTCATCACCAAGTGTCTCCC
CATCCCCACCCTTCCCCATGTTATGGCTTTCCTCCTCTTAGTTCATCAGTGTGCCTCTTTTT
AAACTAGGGAAAACAAGTAAAAGTTGCAAAATTGGANNNNTCTTGTTCTTACATGTCATACT
GTGGGCCATTGAGAATCTTTTGAATAAATTAATTTTAACTCTCCCTTCCCATACCTATTATC
TTACATATTAACAAATGGTATTAACAAATGGGGAAAATGGCCAAATGGAGAAAATGCAAGGA
AATAGACAGTTCATTCTTTGATAAATAAAAATGAAAATAAATCCTATGGCTCTTCTAAAA
AGAAAGTTAATACTATTGTATTAGTCAGTGTTCTTTATTGTCATTTATACTTTCAGTGTTTA
GGGGACCAGTCTGCTGCATTGGTGGGACAAATGTGCTTCCAGATTGGACAAGCCAAAAATAC
GTGAGTTTAAGAAACAGACTTAAAAACCAATGCTGTTTGTTTTTCTACTTGGTGCTTTGA
ATAAGGAAAAGCTTTTGAAGTTCATCCAGGATGAAAATCAATAGCTTAATAGCTCCAATATG
CATATATACACTTTTTACCATTTTTTATATCTTTAAATAAAATACAAAA
TGCCATATATATGCACACTGATGAAGCTTATAAAGACCTAAATTTGTAGGCTGGGCGCGG Exons 10 and 11:
TTATTTGCTTTCAATAAAATTGTCTTCTATTCATTCTCCCTTCAACCATAGGTATGGAACAG
GATGTTTCTTACTATGT [A/G] ATACAGGCCATAAGGTTGGTTTTTAAATTAAAAAATTGA
TTTAAAAGTCTAAGTTCATCTAAATAATGCTTGAACATAATTTACTATTAAACAACTTTTAG
TCTTTAGCTTTTACTTAATCTTTATCAGGGTTTAATTTAGAGCTCAATACAAAATTTGAATC
GTTCTAATAAGAACCATTTTAGACTCTTTGAATTTTATATGTGTGTTTTTAATTGTGCTGGG
GGGAAATCTAGACTGAGACCTCATCAAATTCTTAATGCAAATCTAATTTGAAACAAGGAATA
AACTTTTTATACAGCTTAAATGTGTTCTTAATTCTGATCGTTTTGACTGTAAGGATTTATTT
TAAAAATTGGTTTATTGATTGCATTATTTTGTACCTATGTTATTTTAACTTTAAAAAAAGT
TCTCATGTTATCTTTTCATTTTCCACTACTGAAATCTTTTTTTTTTCTTTCTTACAGTGTGT
ATTTTCTGATCATGGCCTTCTCACCACAGTGGCTTACAAACTTGGCAGAGACAAACCAGTAT
ATTATGCTTTGGAAGTAAGTTCTTTTTAATCAATATGGATAATATGACAAACATTCAAAGCT
AATAAAAATCACAGAGTTTTCTAACACTTTTCTGGTAAATCTTAATACAGAGGACTCAAAAA
GTTCTGCTTTCTTGGCATTTGATTGAGTTGAAGGAACCTGAAACTGATCTGGGTGTCAGGAC
TCACAGGAGACCTTGATTAGATTGGTTCCTCAGTTCTTATGCCAATTAATCATGTCACCTTA
GGCATATTACTTGAGAGCTCTACAATGTGAGGTTTTTTTTTTTTATCTCTAAAGTTTAAT
CGGATTAACGTGCTCTCTAACATTTCTTTCATCTTGAAAATTCTTTGATTTTATAAATAAAA
TGCTCCAGTGTTCCAAAGAGAACCCTGGGCACAAATAGGCAGAACAACTCTCTTCACTTGTC
TCCTCATAAAAATAAATTTTGTGTAACATTTTGATATAGAAAGAAAGCGACGAGATTTATG
CCACTTATCACTGGAAACATTTGTTTCAAACATTTTTGTATGTTATAGTAGGAATATGCCAG
CCTAAGCCTATA

Figure 7B

Exon 12:
TTTTATTAGTGACTTAGATAAAACTATGTTTGTATTAGAAGACCTAGTTTACATATTTGTCG
GAGTCTCAAAATGGAAACTGAATTCTGTCCATCTGATTGTGTCATACACAGAATATGCTCAA
TAAAAACCTTGGATAGTGATAAAATATATTCTGTCTTGAATTCCTTTTTTTCTTTAGGGTTC
TGTAGCTATAGCTGGTGCTGTTATTCGCTGGCTAAGAGACAATCTTGGAATTATAAAGACCT
CAGAAGAAATTGGTGAGTGTGTTCTAACAAAAG [G/T] TTAGAAAATCTGAAAAATGACACA
TTTCAGTATTTTATCTCTGCAAAGTAAATATCGATGCTTTGCCCCAAATGTGAT Exon 13:
CCAGTTGTGTGATTTTTGTTTTGTTTTGTTTTAATGTTAGAAAAACTTGCTAAAGAAGTAGG
TACTTCTTATGGCTGCTACTTCGTCCCAGCATTTTCGGGGTAATATGCACCTTATTGGGAGC
CCAGCGCAAGAGGGTAAGTATTGAAAATATGGAGTGCTTTTGGGGATCTTGATTTAT Exons 14 and 15:
TGTAAAACGACGGCCAGTTGATTATGTCCAATTTTCTCTTCCTGGACATTTCTGTCTACCAA
ATTTGACCTTTTCATATTTGAGATATTTCAAATTGATTGGTTTATATCATTCTAATCTGAAA
ATCTTTGTGCGTATTTTAGGATAATCTGTGGACTCACTCAGTTCACCAATAAATGCCATAT
TGCTTTTGCTGCATTAGAAGCTGTTTGTTTCCAAACTCGAGAGGTAACAAATATGGGCCTGT
TTTCTTGTACTTAGTTCACTTTTATCACTCTTAAGTTATATGTTAACACCCGAGATTTATTC
AGTACTGAAAATGTAGTTAATCAAATATTAAGGCTGCCTAAATACTAATCTAAATATAAGCA
GGGTTTTCCCCCTTTTTCCAGCTGTCATTACCTTCTAAGTTCCTGTTCCCTGTCAGGCACTG
GGAAATTTATGGTTGTGGGGAGGCTGAGTGGCACACATTAGGCAAAGGAAACAGCACAAACA
TAGGCATCaAGGCAGAAAAACAGGGTGCAAAATAGAGTTGTATAGCTTAGCTGAATATCAAG
GTGAATGCAGAGGTGTAGTGAGAGAAAAGGTTGGCTGTGACCAGATCAAAGAGGGCTTAGAA
GACCAGAATAAGAAGTCTCAATTTATTCCATAGGCTCTTGGAAGCTCTTGAGAGTTTCTGAG
TGGAGGATTGCCATTTTCAGAGATGTTACTATGAAATAGATTTATAACATTAATTGCACTGG
TTTATTTAAGATTTTGGATGCCATGAATCGAGACTGTGGAATTCCACTCAGTCATTTGCAGG
TAGATGGAGGAATGACCAGCAACAAAATTCTTATGCAGCTACAAGCAGACATTCTGTATATA
CCAGTAGGTTAGTAAGTCTTCATTCCTTTAAACTCCCAGAGTAATGTTTCTTGTGGAATAAC
TAGTTCTTTGGG Exon 16:
TGTAAAACGACGGCCAGTTCCCAGAGTAATGTTTCTTGTGGAATAACTAGTTCTTTGGGCAT
ATGTAACCACAAAGATATTGATGGAACTCTCTCTCCTCAGTGAAGCCCTCAATGCCCGAAAC
CACTGCACTGGGTGCGGCTATGGCGGCAGGGGCTGCAGAAGGAGTCGGCGTATGGAGTCTCG
AACCCGAGGATTTGTCTGCCGTCACGATGGAGCGGTTTGAACCTCAGATTAATGCGGAGGGT
ACATTTAAAGAATGAAATGTTCAGTGATATACTGTGAAAACGACCTTAGTGCACGGGAGTTT
TGTTTTTCTGTTTAGTTAAAAGTTAAGGAACCAAGTAAAATAGTAAATGTTATCATTGCAGA
TTCGGCTGCCAAGCATATTGGGCTTTACTGAATAAATGTGAATGAGAGAAATCGTTGCTTAT
CAAAAGAACTTCTAAAATCACTTTTTAAAAATCATT Exon 17:
TGTAAAACGACGGCCAGTAGCCCTACTGCAGTTTAATGTGTCAATAATTTGTCAAGAATGTT
GAGTGATCATAAGTATGGTACTAAGAACATCTCAGCAAACTACCTTTCGTTATGTGTTTTTT
CTACCTTCTAATTCTAGAAAGTGAAATTCGTTATTCTACATGGAAGAAAGCTGTGATGAAGT
CAATGGGTTGGGTTACAACTCAATCTCCAGAAAGTGGTAAAAATGTTTTTGTTTATTATTGT
CACATTTTCTTAGTATATTAAATAGTTATTTAAGTATCTAGGCATTTACACATAGCCAGGCT
GCTCTGAAGAAAAGCATTATCATATGTCCAGAGATTCTGACATTTTGAAAACACTTTAAAGT
TCTAAACACAAAATGTAAATTATCAGGTGT

Figure 7C

Exon 18:
TGTAAAACGACGGCCAGTTGGTTTGGTTTGCTTGACTGGAATCTCTTCTGCTTGGATGACCA
CAGGTGACCCTAGTATCTTCTGTAGTCTGCCCTTGGGCTTTTTTATAGTGAGTAGCATGGTA
ATGTTAATCGGAGCAAGGTACATCTCAGGTTAGTTACTCTTTAAATTAGACAACTCTATTAG
TTAGCTTTAATGTTTTCGTGTATAACTTAGCAGAAATTTTTCAGTGTTTTTCATTCTTTCTG
TGTCTAGGAAGCTGGAAAATCAATTAAAGGTCTAATTAGTTAGACCAATTAATCTTTGGGGG
CAGTTAGAAGTAAGAACTGTGACTCTGCTTACCCTTTTTAAATTTTTAATGTGATGACTTCT
TTAAGAGGGACTACATTCTGCTGTCAGCTGCAGCAATAAGCAAAAGTGAAAATACTAATATT
TAAATGACAGGACTTTCAGACTGACTGCTGAAAGTTAAAGTATACTT Exon 19:
AAAATTACTGGCTTAAATGGAAATGATGCTTCTTATTCTGTATGTTCCCATGAAAGTGAAAC
TTAAAAAAAAATTCATGATTAGGGTTTCATGAAAAGGCCTTGTTTCTATGAAAATTGAGAC
AGGTTGCATCTCTCTAAGCTAAAAGATGGGCTATGTGTCTAGAGTCTTAGACTTCTAAAATG
CATGTGGTCACTATATGTAGGTTATCTCTTCGGTGACATACACTGCAATTTGAGAGGGCTGG
AAATTGTTTGCCTTGGTAAACGATTAGCAACAGTGGCAATATTTGTTAATTTTGGAATTGGC
CCTGTTTGTTGCATTTTAATTGTGAGGCATGATTTAGAAATCATATGGACTTTCTAGCTTAA
TAAATGATTGAATCATCTGCATTGCTTTAACTCCTGAATTGTATGCATGTATTATTGACATA
TATGGTTTTTGTTCCCCATTTCAGGTATTCCATAAAACCTACCAACTCATGGATTCCCAAGA
TGTGAGCTTTTTACATAATGAAAGAACCCAGCAATTCTGTCTCTTAATGCAATGACACTATT
CATAGACTTTGATTTTATTTATAAGCCACTTGCTGCATGACCCTCCAAGTAGACCTGTGGCT
TAAAATAAAGAAAATGCAGCAAAAGAATGCTATAGAAATATTTGGTGGTTTTTTTTTTTT
TAAACATCCACAGTTAAGGTTGGGCCAGCTACCTTTGGGGCTGACCCCCTCCATTGCCATAA
CATCCTGCTCCATTCCCTCTAAGATGTAGGAAGAATTCGGATCCTTACCATTGGAATCTTCC
ATCGAACATACTCAAACACTTTTGGACCAGGATTTGAGTCTCTGCATGACATATACTTGATT
AAAAGGTTATTACTAACCTGTTAAAAATCAGCAGCTCTTTGCTTTTAAGAGACACCCTAAAA
GTCTTCTTTTCTACATAGTTGAAGACAGCAACATCTTCACTGAATGTTTGAATAGAAACCTC
TACTAAATTATTAAAATAGACATTTAGTGTTCTCACAGCTTGGATATTTTTCTGAAAAGTTA
TTTGCCAAAACTGAAATCCTTCAGATGTTTTCCATGGTCCCACTAATTATAATGACTTTCTG
TCTGGGTCTTATAGGAAAAGATACTTTCTTTTTCTTCCATCTTTCCTTTTTATATTTTTA
CTTTGTATGTATAACATACATGCCTATATATTTATACACTGAGGGAGCCCATTTATAAATA
AAGAGCACATTATATTCAGAAGGTTCTAACAGGG

Figure 7D

Table 1. Characteristics of Carriers of the N288D GK Gene Mutation and of Their Unaffected Relatives

| | Men | | | Women | | |
|---|---|---|---|---|---|---|
| | N288D carriers | Unaffected relatives | p | N288D carriers | Unaffected relatives | p |
| N | 18 | 18 | | 14 | 14 | |
| Age (years) | 46.4±14.2 | 42.0±18.8 | 0.32 | 44.9±13.5 | 43.7±17.8 | 0.87 |
| Uncorrected triglyceride (mmol/L)[1] | 6.26±1.13 | 2.05±0.54 | <0.0001 | 2.84±1.20 | 1.30±0.65 | 0.0002 |
| Glycerol (mmol/L) | 3.99±0.71 | 0.10±0.04 | <0.0001 | 0.54±0.14 | 0.10±0.02 | <0.0001 |
| Corrected triglyceride (mmol/L)[1] | 2.27±0.75 | 1.95±0.53 | 0.01 | 2.31±1.22 | 1.19±0.67 | 0.03 |
| Free fatty acid (mmol/L) | 0.77±0.22 | 0.57±0.25 | 0.13 | 1.29±0.35 | 0.76±0.17 | 0.0004 |
| Fasting glucose (mmol/L) | 5.2±0.74 | 4.8±0.31 | 0.02 | 5.0±0.7 | 4.6±0.3 | 0.10 |
| 2h glucose following OGTT (mmol/L) | 7.9±3.1 | 5.8±1.6 | 0.62 | 7.0±6.1 | 5.0±2.1 | 0.04 |
| Fasting insulin (mU/L)[1] | 13.3±14.0 | 15.1±14.8 | 0.01 | 12.2±13.1 | 9.0±3.4 | 0.60 |
| Waist girth (cm) | 97.7±9.3 | 88.1±12.3 | 0.03 | 88.5±3.8 | 79.8±5.8 | 0.03 |
| Body mass index (kg/m²) | 27.9±4.1 | 24.9±3.9 | 0.01 | 28.1±5.5 | 23.1±2.3 | 0.001 |
| %Total body fat | 27.1±7.2 | 22.9±7.6 | | 46.8±8.1 | 33.9±11.3 | 0.001 |

(1) Geometric mean, p after log transformation.

Figure 8

Table 2. Fasting plasma glycerol concentration (mmol/L) in the initial cohort of 1056 individuals, by risk factor of glucose intolerance and diabetes mellitus

|  |  |  | No. | Glycerol geometric mean ± SD | p |
|---|---|---|---|---|---|
| Gender | | | | | |
| | men | | 717 | 0.065 ± 0.081 | |
| | women | - premenopaused | 137 | 0.071 ± 0.093 | <0.0001 |
| | | - menopaused | 202 | 0.099 ± 0.085 | |
| Age (Y) | | | | | |
| | | <50 | 486 | 0.071 ± 0.082 | |
| | | 50 - 60 | 408 | 0.076 ± 0.106 | 0.0015 |
| | | >60 | 165 | 0.083 ± 0.053 | |
| Fasting glucose (mmol/L) | | | | | |
| | | < 5.2 | 449 | 0.068 ± 0.080 | |
| | | 5.2 - 5.9 | 336 | 0.070 ± 0.090 | <0.0001 |
| | | 6.0 - 6.9 | 271 | 0.090 ± 0.100 | |
| Fasting insulin (UI) | | | | | |
| | | <15 | 637 | 0.067 ± 0.082 | 0.02 |
| | | ≥15 | 419 | 0.086 ± 0.101 | |
| 2 hours glucose (mmol/L) | | | | | |
| | | <7.8 | 572 | 0.062 ± 0.071 | |
| | | 7.8 - 11.0 | 283 | 0.081 ± 0.101 | <0.0001 |
| | | ε11.1 | 201 | 0.102 ± 0.110 | |
| Triglyceride (mmol/L) | | | | | |
| | | ≤ 2.2 | 389 | 0.057 ± 0.062 | <0.0001 |
| | | >2.2 | 667 | 0.082 ± 0.103 | |
| Free fatty acid (mmol/L) | | | | | |
| | | < 0.6 | 589 | 0.066 ± 0.054 | <0.0001 |
| | | ε0.6 | 467 | 0.111 ± 0.112 | |
| Body mass index (kg/m2) | | | | | |
| | | ≤ 27 | 428 | 0.060 ± 0.087 | <0.0001 |
| | | >27 | 628 | 0.079 ± 0.097 | | p value from a one-way ANOVA

Figure 9

Table 3. Multivariate analysis of the relationships of fasting plasma glycerol concentration with impaired glucose tolerance (2h glucose 7,8-11,0 mmol/L following a 75 g oral load) before and after adjustment for covariates identified in

|  | Model 1 | Model 2 | Model 3 | Model 4 |
|---|---|---|---|---|
| Glycerol (log) | | | | |
| ß | 1.75 | 1.62 | 1.46 | 0.77 |
| Odds ratio | 5.76 | 5.42 | 4.33 | 2.46 |
| p | <0.0001 | <0.0001 | <0.0001 | 0.01 |
| Triglyceride (log) | | | | |
| ß |  | 0.54 | 0.35 | 0.12 |
| Odds ratio |  | 1.75 | 1.42 | 1.12 |
| p |  | 0.02 | 0.11 | 0.63 |
| Body mass index (kg/m$^2$) | | | | |
| ß |  |  | 0.10 | 0.05 |
| Odds ratio |  |  | 1.10 | 1.05 |
| p |  |  | <0.0001 | 0.01 |
| Fasting insulin (log) | | | | |
| ß |  |  |  | 0.57 |
| Odds ratio |  |  |  | 1.31 |
| p |  |  |  | 0.39 |
| Fasting glucose (mmol/L) | | | | |
| ß |  |  |  | 1.13 |
| Odds ratio |  |  |  | 2.65 |
| p |  |  |  | <0.0001 |
| Free fatty acid (log) | | | | |
| ß |  |  |  | 1.62 |
| Odds ratio |  |  |  | 4.33 |
| p |  |  |  | 0.007 |

Odds ratios are expressed as the increase in the risk of 2h glucose 7.8-11.0 mmol/L following a 75 g oral load, associated with a 1-SD increase in the variables studied. ß denotes the standardized estimate which is the parameter estimate of each variable in the multivariate logistic model. All models included age and gender as covariates. Otherwise, only the variables included in each model are shown. Subjects with severe hyperglycerolemia due to the N288D mutation in the

Figure 10

SEQUENCE LISTING

```
<160> NUMBER OF SEQ ID NOS: 23

<210> SEQ ID NO 1
<211> LENGTH: 60
<212> TYPE: DNA
<213> ORGANISM: Unknown
<220> FEATURE:
<223> OTHER INFORMATION: Partial nucleic acid sequence of the GK gene
      comprising a polymorphic site at nucleotide
      position 13 of exon 3

<400> SEQUENCE: 1
atgccttctt ttgtcaaaga tgggtggaac argaccctaa ggaaattcta cattctgtct      60

<210> SEQ ID NO 2
<211> LENGTH: 48
<212> TYPE: DNA
<213> ORGANISM: Unknown
<220> FEATURE:
<223> OTHER INFORMATION: Partial nucleic acid sequence of the GK gene
      comprising a polymorphic site at nucleotide
      position 17 of intron 8

<400> SEQUENCE: 2
taatggtaaa aaacaaacaa amaaacaaaa aacacaccaa aaaaccaa                  48

<210> SEQ ID NO 3
<211> LENGTH: 94
<212> TYPE: DNA
<213> ORGANISM: Unknown
<220> FEATURE:
<223> OTHER INFORMATION: Partial nucleic acid sequence of the GK gene
      comprising a  polymorphic site at nucleotide
      position 29 of exon 10

<400> SEQUENCE: 3
ttcattctcc cttcaaccat aggtatggaa caggatgttt cttactatgt ratacaggcc      60
ataaggttgg tttttaataa aaatgattaa gtca                                 94

<210> SEQ ID NO 4
<211> LENGTH: 58
<212> TYPE: DNA
<213> ORGANISM: Unknown
<220> FEATURE:
<223> OTHER INFORMATION: Partial nucleic acid sequence of the GK gene
      comprising a polymorphic site at nucleotide
      position 22 of intron 12

<400> SEQUENCE: 4
gaaattggtg agtgtgttct aacaaaagkt tagaaaatct gaaaaatgac acatttca        58

<210> SEQ ID NO 5
<211> LENGTH: 8079
```

<210> TYPE: DNA
<213> ORGANISM: Unknown
<220> FEATURE:
<223> OTHER INFORMATION: Glycerol kinase gene
<220> FEATURE:
<221> NAME/KEY: misc_feature
<222> LOCATION: 2214, 2215, 2216, 2217
<223> OTHER INFORMATION: n = A,T,C or G

<400> SEQUENCE: 5

```
ggttcagcgg acgcgcgcgg cctcggtctc tggactcgtc acctgcccct ccccctcccg      60
ccgccgtcac ccaggaaacc ggccgcaatc gccggccgac ctgaagctgg tttcatggca     120
gcctcaaaga aggcagtttt ggggccattg gtggggcgg tggaccaggg caccagttcg     180
acgcgctttt tggtgagccc ggggtgacat gtgaagaggc gctgagctgt aaaacgacgg     240
ccagtcatcc ttgatatctg cctgcatttt tacattaata ttacaatatc tttttcaggt     300
tttcaattca aaaacagctg aactacttag tcatcatcaa gtagaaataa acaagagtt      360
cccaagagaa gggtatgttt cctaatttaa tatgtaaaga cacattatgt ttgttagtcc     420
atctcaccca acttgcccca atgccttctt ttgtcaaaga tgggtggaac argaccctaa     480
ggaaattcta cattctgtct atgagtgtat agagaaaaca tgtgagaaac ttggacagct     540
caatattgat atttccaaca taaaaggtat tttagtagaa tattttaccc acatgtaaaa     600
cgacggccag ttgagagctg ttttcctgaa gtagttccta cttgttaaat ttttgacttc     660
cttctgttta actttctctt taaagctatt ggtgtcagca accagaggga aaccactgta     720
gtctgggaca agataactgg agagcctctc tacaatgctg tgggtaagct gtcatgcatg     780
gatgtcaaat gtagggcctt tcttcacatt gcaatgtaaa acgacggcca gttccttgat     840
agtgatttca gtaagttctt atttttttaa atgaagtttt tcatgtatat tattttattt     900
tggtctatag tgtggcttga tctaagaacc cagtctaccg ttgagagtct tagtaaaaga     960
attccaggaa ataataactt tgtcaaggta agaatttctt cagaagtata ctataagaat    1020
gtttcttttt ttaaaaaaag tttgcagatt tcactagaaa gaagcatctt atggtacaat    1080
agttatttga tacaatttat agaatctttt tcccggataa ttgaggcctg taaaacgacg    1140
gccagtttct tttgttttggt ggttttgttt taaactgtta cacttttcat ttgctaactg    1200
aacttcacaa ctgcttttag tccaagacag gccttccact tagcacttac ttcagtgcag    1260
tgaaacttcg ttggctcctt gacaatgtga gaaaagttca aaaggccgtt gaagaaaaac    1320
gagctctttt tgggactatt gattcatggc ttatttgggt atgtttaaat ataatggata    1380
tatggagaat ttttttcagaa attttttcta gactgccttg cctattgttt ctactagcag    1440
gtcagacttt ttaattagca tgtaaaacga cggccagttg tgctctgctg attatgaccc    1500
ttaacaatat gtaaattaaa ttgccaataa gtacaaattt aacctgattt ttttactctg    1560
cctagagttt gacaggagga gtcaatggag gtgtccactg tacagatgta acaaatgcaa    1620
gtaggactat gcttttcaac attcattctt tggaatggga taaacaactc tgcgagtaag    1680
ttctgttttg ctctaaatat agttttccca atacactacc tatttataac cgaaatctta    1740
atattttcag atgtcagtgg agcatgtaaa acgacggcca gtacagtgtt aaatacccaa    1800
tcttcttgtt tttcagatt tttggaattc caatggaaat tcttccaaat gtccggagtt    1860
cttctgagat ctatggccta atggtaaaaa acaaacaaam aaacaaaaaa cacaccaaaa    1920
aaccaaaaaa caaacaaaaa aaaacctaat aattaaagtt ttttattac aaaacaagtt    1980
tactattcat aattcaaaag tcaactgtgt tatgttttgt gacttaaaaa ctttacagtc    2040
```

```
cttttttacaa tggaaagctg gggccttgga aggtgtgcca atatctgggg taagtttcat  2100
caccaagtgt ctccccatcc ccacccttcc ccatgttatg gctttcctcc tcttagttca  2160
tcagtgtgcc tcttttttaaa ctagggaaaa caagtaaaag ttgcaaaatt ggannnntct  2220
tgttcttaca tgtcatactg tgggccattg agaatctttt gaataaatta attttaactc  2280
tcccttccca tacctattat cttacatatt aacaaatggt attaacaaat ggggaaaatg  2340
gccaaatgga gaaatgcaa ggaaatagac agttcattct ttgataaata aaaatgaaa  2400
aataaatcct atggctcttc taaaaagaaa gttaatacta ttgtattagt cagtgttctt  2460
tattgtcatt tatactttca gtgtttaggg gaccagtctg ctgcattggt gggacaaatg  2520
tgcttccaga ttggacaagc caaaatacg tgagtttaag aaacagactt aaaaaccaat  2580
gctgttttgt tttttctact tggtgctttg aataaggaaa agcttttgaa gttcatccag  2640
gatgaaaatc aatagcttaa tagctccaat atgcatatat acactttta ccattttttt  2700
atatctttaa ataaaataca aaatgccata tatatgcaca ctgatgaagc ttataaagac  2760
ctaaatttgt aggctgggcg cggttatttg cttttcaataa aattgtcttc tattcattct  2820
cccttcaacc ataggtatgg aacaggatgt ttcttactat gtratacagg ccataaggtt  2880
ggttttttaa attaaaaaat tgatttaaaa gtctaagttc atctaaataa tgcttgaaca  2940
taatttacta ttaaacaact tttagtcttt agcttttact taatctttat cagggtttaa  3000
tttagagctc aatacaaaat ttgaatcgtt ctaataagaa ccattttaga ctctttgaat  3060
tttatatgtg tgtttttaat tgtgctgggg ggaaatctag actgagacct catcaaattc  3120
ttaatgcaaa tctaatttga aacaaggaat aaacttttta tacagcttaa atgtgttctt  3180
aattctgatc gttttgactg taaggattta ttttaaaaat tggtttattg attgcattat  3240
tttgtaccta tgttatttta actttaaaaa aaagttctca tgttatcttt tcattttcca  3300
ctactgaaat cttttttttt tctttcttac agtgtgtatt ttctgatcat ggccttctca  3360
ccacagtggc ttacaaactt ggcagagaca aaccagtata ttatgctttg gaagtaagtt  3420
cttttttaatc aatatggata atatgacaaa cattcaaagc taataaaaat cacagagttt  3480
tctaacactt ttctggtaaa tcttaataca gaggactcaa aaagttctgc tttcttggca  3540
tttgattgag ttgaaggaac ctgaaactga tctgggtgtc aggactcaca ggagaccttg  3600
attagattgg ttcctcagtt cttatgccaa ttaatcatgt caccttaggc atattacttg  3660
agagctctac aatgtgaggt ttttttttttt tttatctcta aagtttaatc ggattaacgt  3720
gctctctaac atttctttca tcttgaaaat tctttgattt tataaataaa atgctccagt  3780
gttccaaaga gaaccctggg cacaaatagg cagaacaact ctcttcactt gtctcctcat  3840
aaaaataaat tttgtgtaac atttttgatat agaaagaaa gcgacgagat ttatgccact  3900
tatcactgga acatttgtt tcaaacattt ttgtatgtta tagtaggaat atgccagcct  3960
aagcctatat tttattagtg acttagataa aactatgttt gtattagaag acctagttta  4020
catatttgtc ggagtctcaa aatggaaact gaattctgtc catctgattg tgtcatacac  4080
agaatatgct caataaaaac cttggatagt gataaaatat attctgtctt gaattccttt  4140
ttttctttag ggttctgtag ctatagctgg tgctgttatt cgctggctaa gagacaatct  4200
tggaattata aagacctcag aagaaattgg tgagtgtgtt ctaacaaaag kttagaaaat  4260
ctgaaaaatg acacatttca gtatttatc tctgcaaagt aaatatcgat gctttgcccc  4320
aaatgtgatc cagttgtgtg attttttgttt tgttttgttt taatgttaga aaacttgct  4380
aaagaagtag gtacttctta tggctgctac ttcgtcccag cattttcggg gtaatatgca  4440
```

```
ccttattggg agcccagcgc aagagggtaa gtattgaaaa tatggagtgc tttggggat      4500 cttgatttat tgtaaaacga cggccagttg attatgtcca attttctctt cctggacatt      4560
tctgtctacc aaatttgacc ttttcatatt tgagatattt caaattgatt ggtttatatc      4620
attctaatct gaaaatcttt gtgcgtattt ttaggataat ctgtggactc actcagttca      4680
ccaataaatg ccatattgct tttgctgcat tagaagctgt ttgtttccaa actcgagagg      4740
taacaaatat gggcctgttt tcttgtactt agttcacttt tatcactctt aagttatatg      4800
ttaacacccg agatttattc agtactgaaa atgtagttaa tcaaatatta aggctgccta      4860
aatactaatc taaatataag cagggttttc ccccttttc cagctgtcat taccttctaa      4920
gttcctgttc cctgtcaggc actgggaaat ttatggttgt ggggaggctg agtggcacac      4980
attaggcaaa ggaaacagca caaacatagg catcaaggca gaaaacagg gtgcaaaata      5040 gagttgtata gcttagctga atatcaaggt gaatgcagag gtgtagtgag agaaaaggtt      5100
ggctgtgacc agatcaaaga gggcttagaa gaccagaata agaagtctca atttattcca      5160
taggctcttg gaagctcttg agagtttctg agtggaggat tgccattttc agagatgtta      5220
ctatgaaata gatttataac attaattgca ctggtttatt taagattttg gatgccatga      5280
atcgagactg tggaattcca ctcagtcatt tgcaggtaga tggaggaatg accagcaaca      5340
aaattcttat gcagctacaa gcagacattc tgtatatacc agtaggttag taagtcttca      5400
ttcctttaaa ctcccagagt aatgtttctt gtggaataac tagttctttg ggtgtaaaac      5460
gacggccagt tcccagagta atgtttcttg tggaataact agttctttgg gcatatgtaa      5520
ccacaaagat attgatggaa ctctctctcc tcagtgaagc cctcaatgcc cgaaaccact      5580
gcactgggtg cggctatggc ggcaggggct gcagaaggag tcggcgtatg gagtctcgaa      5640
cccgaggatt tgtctgccgt cacgatggag cggtttgaac ctcagattaa tgcggagggt      5700
acatttaaag aatgaaatgt tcagtgatat actgtgaaaa cgaccttagt gcacgggagt      5760 tttgttttc tgtttagtta aaagttaagg aaccaagtaa aatagtaaat gttatcattg      5820
cagattcggc tgccaagcat attgggcttt actgaataaa tgtgaatgag agaaatcgtt      5880
gcttatcaaa agaacttcta aaatcacttt ttaaaaatca tttgtaaaac gacggccagt      5940
agccctactg cagtttaatg tgtcaataat ttgtcaagaa tgttgagtga tcataagtat      6000
ggtactaaga acatctcagc aaactacctt tcgttatgtg ttttttctac cttctaattc      6060
tagaaagtga aattcgttat tctacatgga agaaagctgt gatgaagtca atgggttggg      6120
ttacaactca atctccagaa agtggtaaaa atgttttgt ttattattgt cacattttct      6180
tagtatatta aatagttatt taagtatcta ggcatttaca catagccagg ctgctctgaa      6240
gaaaagcatt atcatatgtc cagagattct gacattttga aaacacttta aagttctaaa      6300
cacaaaatgt aaattatcag gtgttgtaaa acgacggcca gttggtttgg tttgcttgac      6360
tggaatctct tctgcttgga tgaccacagg tgaccctagt atcttctgta gtctgccctt      6420 gggcttttt atagtgagta gcatggtaat gttaatcgga gcaaggtaca tctcaggtta      6480
gttactcttt aaattagaca actctattag ttagctttaa tgttttcgtg tataacttag      6540
cagaaatttt tcagtgtttt tcattctttc tgtgtctagg aagctggaaa tcaattaaa      6600 ggtctaatta gttagaccaa ttaatctttg ggggcagtta gaagtaagaa ctgtgactct      6660 gcttacccctt tttaaatttt taatgtgatg acttctttaa gagggactac attctgctgt      6720
cagctgcagc aataagcaaa agtgaaaata ctaatatta aatgacagga ctttcagact      6780
```

```
gactgctgaa agttaaagta tacttaaaat tactggctta aatggaaatg atgcttctta   6840
ttctgtatgt tcccatgaaa gtgaaactta aaaaaaaaat tcatgattag ggtttcatga   6900
aaaggccttg tttctatgaa aattgagaca ggttgcatct ctctaagcta aaagatgggc   6960
tatgtgtcta gagtcttaga cttctaaaat gcatgtggtc actatatgta ggttatctct   7020
tcggtgacat acactgcaat ttgagagggc tggaaattgt ttgccttggt aaacgattag   7080
caacagtggc aatatttgtt aattttggaa ttggccctgt ttgttgcatt ttaattgtga   7140
ggcatgattt agaaatcata tggactttct agcttaataa atgattgaat catctgcatt   7200
gctttaactc ctgaattgta tgcatgtatt attgacatat atggtttttg ttccccattt   7260
caggtattcc ataaaaccta ccaactcatg gattcccaag atgtgagctt tttacataat   7320
gaaagaaccc agcaattctg tctcttaatg caatgacact attcatagac tttgatttta   7380
tttataagcc acttgctgca tgaccctcca agtagacctg tggcttaaaa taagaaaat    7440 gcagcaaaaa gaatgctata gaaatatttg gtggtttttt tttttttttaa acatccacag   7500 ttaaggttgg gccagctacc tttggggctg acccccctcca ttgccataac atcctgctcc   7560
attccctcta agatgtagga agaattcgga tccttaccat tggaatcttc catcgaacat   7620
actcaaacac ttttggacca ggatttgagt ctctgcatga catatacttg attaaaaggt   7680
tattactaac ctgttaaaaa tcagcagctc tttgctttta agagacaccc taaaagtctt   7740
cttttctaca tagttgaaga cagcaacatc ttcactgaat gtttgaatag aaacctctac   7800
taaattatta aaatagacat ttagtgttct cacagcttgg atattttttct gaaaagttat   7860 ttgccaaaac tgaaatcctt cagatgtttt ccatggtccc actaattata atgactttct   7920
gtctgggtct tataggaaaa gatactttct tttttcttcc atctttcctt tttatatttt   7980
ttactttgta tgtataacat acatgcctat atatttttata cactgaggga gcccatttat   8040
aaataaagag cacattatat tcagaaggtt ctaacaggg                          8079
```

<210> SEQ ID NO 6
<211> LENGTH: 41
<212> TYPE: PRT
<213> ORGANISM: Unknown
<220> FEATURE:
<223> OTHER INFORMATION: GK N288D mutant

<400> SEQUENCE: 6

Phe Gln Ile Gly Gln Ala Lys Asn Thr Tyr Gly Thr Gly Cys Phe Leu
1               5                   10                  15

Leu Cys Asp Thr Gly His Lys Cys Val Phe Ser Asp His Gly Leu Leu
            20                  25                  30

Thr Thr Val Ala Tyr Lys Leu Gly Arg
        35                  40

<210> SEQ ID NO 7
<211> LENGTH: 41
<212> TYPE: PRT
<213> ORGANISM: Homo sapiens

<400> SEQUENCE: 7

Phe Gln Ile Gly Gln Ala Lys Asn Thr Tyr Gly Thr Gly Cys Phe Leu
1               5                   10                  15

Leu Cys Asn Thr Gly His Lys Cys Val Phe Ser Asp His Gly Leu Leu
            20                  25                  30

Thr Thr Val Ala Tyr Lys Leu Gly Arg
        35                  40

-continued

<210> SEQ ID NO 8
<211> LENGTH: 41
<212> TYPE: PRT
<213> ORGANISM: Unknown
<220> FEATURE:
<223> OTHER INFORMATION: Rat

<400> SEQUENCE: 8

Phe Gln Asp Gly Gln Ala Lys Asn Thr Tyr Gly Thr Gly Cys Phe Leu
1               5                   10                  15

Leu Cys Asn Thr Gly His Lys Cys Val Phe Ser Glu His Gly Leu Leu
            20                  25                  30

Thr Thr Val Ala Tyr Lys Leu Gly Arg
        35                  40

<210> SEQ ID NO 9
<211> LENGTH: 41
<212> TYPE: PRT
<213> ORGANISM: Unknown
<220> FEATURE:
<223> OTHER INFORMATION: Mouse

<400> SEQUENCE: 9

Phe Gln Asp Gly Gln Ala Lys Asn Thr Tyr Gly Thr Gly Cys Phe Leu
1               5                   10                  15

Leu Cys Asn Thr Gly His Lys Cys Val Phe Ser Glu His Gly Leu Leu
            20                  25                  30

Thr Thr Val Ala Tyr Lys Leu Gly Arg
        35                  40

<210> SEQ ID NO 10
<211> LENGTH: 39
<212> TYPE: PRT
<213> ORGANISM: E. coli

<400> SEQUENCE: 10

Val Lys Glu Gly Met Ala Lys Asn Thr Tyr Gly Thr Gly Cys Phe Met
1               5                   10                  15

Leu Met Asn Thr Gly Glu Lys Ala Val Lys Ser Glu Asn Gly Leu Leu
            20                  25                  30

Thr Thr Ile Ala Cys Gly Pro
        35

<210> SEQ ID NO 11
<211> LENGTH: 39
<212> TYPE: PRT
<213> ORGANISM: Pseudomonas aeruginosa

<400> SEQUENCE: 11

Val Glu Pro Gly Gln Ala Lys Asn Thr Tyr Gly Thr Gly Cys Phe Leu
1               5                   10                  15

Leu Met His Thr Gly Asp Lys Ala Val Lys Ser Thr His Gly Leu Leu
            20                  25                  30

Thr Thr Ile Ala Cys Gly Pro
        35

<210> SEQ ID NO 12
<211> LENGTH: 39
<212> TYPE: PRT
<213> ORGANISM: Enterococcus casseliflavus

```
<400> SEQUENCE: 12

Phe Glu Lys Gly Met Ile Lys Asn Thr Tyr Gly Thr Gly Ala Phe Ile
1               5                   10                  15

Val Met Asn Thr Gly Glu Glu Pro Gln Leu Ser Asp Asn Asp Leu Leu
            20                  25                  30

Thr Thr Ile Gly Tyr Gly Ile
        35

<210> SEQ ID NO 13
<211> LENGTH: 41
<212> TYPE: PRT
<213> ORGANISM: Haemophilus influenzae

<400> SEQUENCE: 13

Val His Ala Gly Gln Ala Lys Asn Thr Tyr Gly Thr Gly Cys Phe Met
1               5                   10                  15

Leu Leu His Thr Gly Asn Lys Ala Ile Thr Ser Lys Asn Gly Leu Leu
            20                  25                  30

Thr Thr Ile Ala Cys Asn Ala Lys Gly
        35                  40

<210> SEQ ID NO 14
<211> LENGTH: 39
<212> TYPE: PRT
<213> ORGANISM: Bacillus subtilis

<400> SEQUENCE: 14

Phe Glu Glu Gly Met Gly Lys Asn Thr Tyr Gly Thr Gly Cys Phe Met
1               5                   10                  15

Leu Met Asn Thr Gly Glu Lys Ala Ile Lys Ser Glu His Gly Leu Leu
            20                  25                  30

Thr Thr Ile Ala Trp Gly Ile
        35

<210> SEQ ID NO 15
<211> LENGTH: 41
<212> TYPE: PRT
<213> ORGANISM: Saccharomyces cerevisiae

<400> SEQUENCE: 15

Tyr Lys Pro Gly Ala Ala Lys Cys Thr Tyr Gly Thr Gly Cys Phe Leu
1               5                   10                  15

Leu Tyr Asn Thr Gly Thr Lys Lys Leu Ile Ser Gln His Gly Ala Leu
            20                  25                  30

Thr Thr Leu Ala Phe Trp Phe Pro His
        35                  40

<210> SEQ ID NO 16
<211> LENGTH: 41
<212> TYPE: PRT
<213> ORGANISM: Mycoplasma genitalium

<400> SEQUENCE: 16

Thr Glu Pro Gly Met Val Lys Asn Thr Tyr Gly Thr Gly Cys Phe Val
1               5                   10                  15

Leu Met Asn Ile Gly Asp Lys Pro Thr Leu Ser Lys His Asn Leu Leu
            20                  25                  30

Thr Thr Val Ala Trp Gln Leu Glu Asn
        35                  40
```

```
<210> SEQ ID NO 17
<211> LENGTH: 39
<212> TYPE: PRT
<213> ORGANISM: Enterococcus faecalis

<400> SEQUENCE: 17

Phe Glu Pro Gly Met Val Lys Asn Thr Tyr Gly Thr Gly Ser Phe Ile
1               5                   10                  15

Val Met Asn Thr Gly Glu Glu Pro Gln Leu Ser Lys Asn Asn Leu Leu
            20                  25                  30

Thr Thr Ile Gly Tyr Gly Ile
        35

<210> SEQ ID NO 18
<211> LENGTH: 41
<212> TYPE: PRT
<213> ORGANISM: Mycoplasma pneumoniae

<400> SEQUENCE: 18

Val Glu Pro Ala Met Val Lys Asn Thr Tyr Gly Thr Gly Cys Phe Met
1               5                   10                  15

Leu Met Asn Ile Gly Asn Glu Leu Lys Tyr Ser Gln His Asn Leu Leu
            20                  25                  30

Thr Thr Val Ala Trp Gln Leu Glu Asn
        35                  40

<210> SEQ ID NO 19
<211> LENGTH: 41
<212> TYPE: PRT
<213> ORGANISM: Synechocystis PCC6803

<400> SEQUENCE: 19

Asp Arg Pro Gly Leu Leu Lys Cys Thr Tyr Gly Thr Gly Ala Phe Leu
1               5                   10                  15

Val Ala Asn Thr Gly Gln Thr Val Thr Arg Ser Gln His Arg Leu Leu
            20                  25                  30

Ser Thr Val Ala Trp Thr Gln Thr Asn
        35                  40

<210> SEQ ID NO 20
<211> LENGTH: 12
<212> TYPE: DNA
<213> ORGANISM: Artificial Sequence
<220> FEATURE:
<223> OTHER INFORMATION: GK gene polymorphism

<400> SEQUENCE: 20
ggacargacc ct                                                           12

<210> SEQ ID NO 21
<211> LENGTH: 16
<212> TYPE: DNA
<213> ORGANISM: Artificial Sequence
<220> FEATURE:
<223> OTHER INFORMATION: GK gene polymorphism

<400> SEQUENCE: 21
aaacaaahaa acaaaa                                                       16

<210> SEQ ID NO 22
<211> LENGTH: 13
<212> TYPE: DNA
```

-continued

```
<213> ORGANISM: Artificial Sequence
<220> FEATURE:
<223> OTHER INFORMATION: GK gene polymorphism

<400> SEQUENCE: 22
actatgtrat aca                                                  13

<210> SEQ ID NO 23
<211> LENGTH: 16
<212> TYPE: DNA
<213> ORGANISM: Artificial Sequence
<220> FEATURE:
<223> OTHER INFORMATION: GK gene polymorphism

<400> SEQUENCE: 23
aacaaaagkt tagaaa                                               16
```

GLYCEROL AS A PREDICTOR OF GLUCOSE TOLERANCE

RELATED APPLICATIONS

This application claims the benefit of U.S. provisional application Serial No. 60/161,141, filed Oct. 22, 1999, the entire teachings of which are incorporated herein by reference.

BACKGROUND OF THE INVENTION

Glycerol kinase (GK) catalyzes the entry of glycerol into the glucose and triglyceride metabolic pathway. Impaired glucose tolerance (IGT) and hypertriglyceridemia are associated with an increased risk of diabetes mellitus (DM) and cardiovascular disease. The relationship between glycerol and the risk of IGT, however, is poorly understood.

SUMMARY OF THE INVENTION

Work described herein details the identification of alterations in the glycerol kinase (GK) gene which result in severe hyperglycerolemia and impaired glucose metabolism and body fat distribution. Glycerol levels are shown to be highly heritable and associated with significant variations in glucose tolerance. This work indicates that glycerol is a potentially significant predictor of the magnitude of glucose tolerance and thus of increased risk of diabetes mellitus (DM) and cardiovascular disease.

Work described herein assessed the association of fasting plasma glycerol concentration with 2-hour glucose following a 75 g oral glucose tolerance test in a cohort of 1056 unrelated French Canadians presenting with a family history of hypertriglyceridemia. The familial resemblance of fasting glycerol in these subjects' families has been estimated, and the GK gene was screened for the presence of mutations.

Family screening in the initial cohort identified 18 individuals with severe hyperglycerolemia (values above 2.0 mmol/L). These individuals were shown to carry a missense mutation (N288D) in exon 10 of the GK gene. Analysis of the biological variables among the N288D carriers led to the observation that variation in glycerolemia was a predictor of impaired glucose metabolism and of abdominal fat accumulation. In the absence of severe hyperglycerolemia, a significant familial resemblance for fasting glycerol concentration (F ratio:6,3; p<0.0001) was observed. Furthermore, multivariate analyses performed in the initial cohort revealed substantial variation in fasting glycerolemia which was associated with significant differences in glucose tolerance, independent of known covariates such as age, gender and body mass index as well as fasting triglyceride, glucose, insulin and free fatty acid concentrations. These results suggest an important genetic connection between glycerol and glucose homeostasis and indicate that assessment of glycerol levels could be a clinically useful tool in the prediction of IGT.

The invention relates to a method of predicting or assisting in the prediction of impaired glucose tolerance, diabetes mellitus, hyperglycerolemia and/or cardiovascular disease in an individual, comprising the steps of obtaining a biological sample from an individual; and assessing the glycerol level in said sample, wherein an increased level of glycerol in said sample as compared with a control sample is predictive of impaired glucose tolerance, diabetes mellitus, hyperglycerolemia and/or cardiovascular disease in the individual. In one embodiment, the increased glycerol level is greater than about 0.08 mmol/L. In another embodiment, the biological sample is a blood sample. In one embodiment, the glycerol level is a plasma glycerol level, and in one embodiment the sample is a fasting sample.

The invention also relates to a method of predicting or assisting in the prediction of impaired glucose tolerance, diabetes mellitus, cardiovascular disease and/or hyperglycerolemia in an individual, comprising the steps of obtaining a nucleic acid sample from an individual; and determining the nucleotide present at nucleotide position 29 of exon 10, wherein presence of a guanine at said position is predictive of impaired glucose tolerance, diabetes mellitus, cardiovascular disease and/or hyperglycerolemia in the individual as compared with an individual having an adenosine at said position.

The invention also relates to a method of predicting or assisting in the prediction of impaired glucose tolerance, diabetes mellitus, cardiovascular disease and/or hyperglycerolemia in an individual, comprising the steps of obtaining a biological sample comprising the glycerol kinase protein or portion thereof from an individual; and determining the amino acid present at amino acid position 288, wherein presence of an aspartate at said position is predictive of impaired glucose tolerance, diabetes mellitus, cardiovascular disease and/or hyperglycerolemia in the individual as compared with an individual having an asparagine at said position.

The invention further relates to a method of identifying an agent which is an agonist of glycerol kinase, comprising the steps of providing a recombinant host cell of the invention; contacting said host cell with an agent to be tested; and assessing the ability of the agent to increase glycerol kinase activity, wherein an agent which increases glycerol kinase activity is an agonist of glycerol kinase activity. In one embodiment, the step of assessing is performed by determining the level of one or more downstream effects of a glycerol metabolic pathway and comparing said level with a level in an appropriate control.

The invention further relates to a method of predicting or assisting in the prediction of impaired glucose tolerance, diabetes mellitus, cardiovascular disease and/or hyperglycerolemia in an individual, comprising the steps of obtaining a biological sample from an individual; and assessing the level of glycerol kinase gene expression in said sample, wherein a decreased glycerol kinase gene expression level in said sample as compared with a control sample is predictive of impaired glucose tolerance, diabetes mellitus, cardiovascular disease and/or hyperglycerolemia in the individual.

The invention also relates to a method of predicting or assisting in the prediction of impaired glucose tolerance, diabetes mellitus, cardiovascular disease and/or hyperglycerolemia in an individual, comprising the steps of obtaining a biological sample from an individual; and assessing the level of active glycerol kinase in said sample, wherein a decreased level of active glycerol kinase in said sample as compared with a control sample is predictive of impaired glucose tolerance, diabetes mellitus, cardiovascular disease and/or hyperglycerolemia in the individual.

The invention also relates to an isolated nucleic acid molecule comprising SEQ ID NOS: 1–4. The invention further relates to an isolated nucleic acid molecule comprising a portion of SEQ ID NOS: 14, wherein said portion is at least 10 nucleotides in length and wherein said portion comprises a polymorphic nucleotide position occupied by the alternate (non-wildtype) nucleotide. The invention also relates to nucleic acid constructs and recombinant host cells comprising the isolated nucleic acid molecules of the invention. For example, the recombinant host cell can be selected from the group consisting of adipocytes, lymphoblasts and fibroblasts.

The invention further relates to gene products, e.g., mRNA or polypeptides, encoded by the nucleic acid molecules of the invention.

BRIEF DESCRIPTION OF THE DRAWINGS

FIGS. 3A and 3B show the N288D mutation and alignment of the amino acid sequence with the wildtype amino acid sequences from different organisms. FIG. 3A shows the location of the N288D mutation. FIG. 3B shows the alignment of the amino acid sequence with the wildtype amino acid sequences from different organisms (SEQ ID NOS: 6–19). Abbreviations are as follows: pseae, *Pseudomonas aeruginosa*; entca, *Enterococcus casseliflavus*; haein, *Haemophilus influenzae*; bacsu, *Bacillus subtilis*; yeast, *Saccharomyces cerevisiae*; mycge, *Mycoplasma genitalium*; entfa, *Enterococcus faecalis*; mycpn, *Mycoplasma pneumoniae*; syny3, Synechocystis PCC6803. Dashes represent gaps introduced to maximize alignment.

FIGS. 4A and 4B illustrate that among the 18 men carrying the N288D mutation, glycerol was a significant correlate of 2-hour glucose following a 75 g oral load ($r^2$=0.689, p<0.0001) (4A) and waist girth ($r^2$=0.452, p<0.0001) (4B). Five men with previously-diagnosed type 2 diabetes mellitus did not undergo oral glucose tolerance test (OGTT). FIG. 4C shows mean plasma glycerol concentrations (±95% confidence interval) according to the magnitude of glucose tolerance in subjects with severe hyperglycerolemia due to the N288D mutation (N=18), and within the initial cohort (non-GKD, N=1051). NORM defines the category of subjects with normal glucose tolerance (2-hour glucose <7, 8 mmol/L following a 75 g oral glucose absorption). IGT identifies impaired glucose tolerance (2-hour glucose 7.8–11.0 mmol/ L), whereas DM denotes the presence of criteria of type 2 diabetes mellitus (2-hour glucose ≧11.1 mmol/L) during the OGTT.

FIG. 6 shows partial nucleic acid sequences (SEQ ID NOS: 1–4, respectively) of the GK gene comprising specific polymorphic sites, as well as the wild type and alternate nucleotides and the amino acid change, if any.

FIGS. 7A-7D show the nucleic acid sequence of the GK gene (SEQ ID NO: 5). Polymorphic sites are shown in brackets.

FIG. 8 is a table showing characteristics of carriers of the N288D GK gene mutation and of their unaffected relatives.

FIG. 9 is table showing the fasting plasma glycerol concentration by risk factor of glucose intolerance and diabetes mellitus.

FIG. 10 is a table showing a multivariate analysis of the relationships of fasting plasma glycerol concentration with impaired glucose tolerance.

DETAILED DESCRIPTION OF THE INVENTION

Figure 1A:
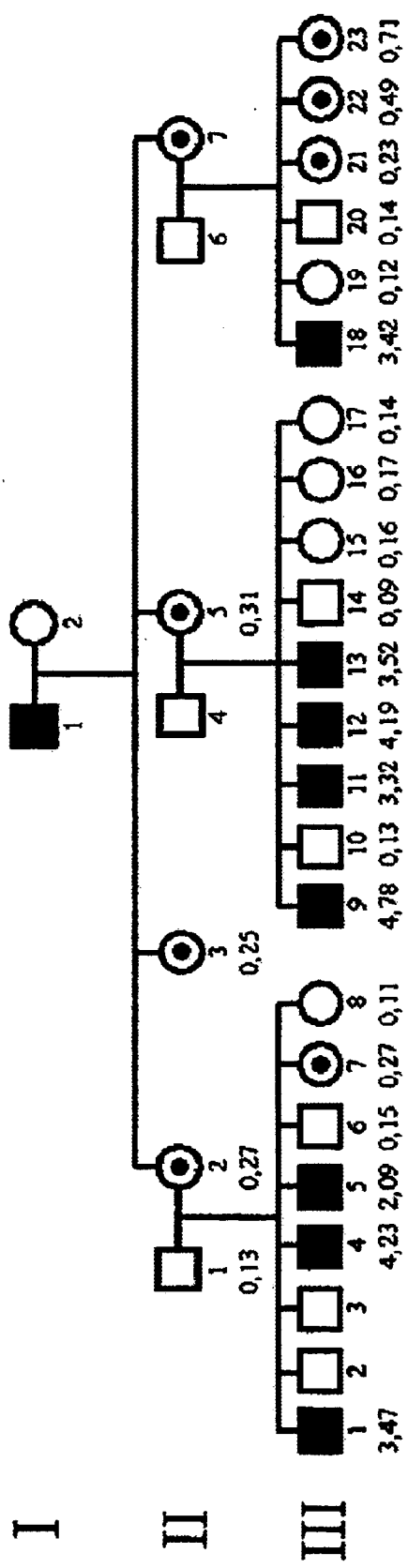
FIGS. 1A–1C show pedigree drawings for three families with hyperglycerolemia. Open squares indicate unaffected males; filled squares indicate hyperglycerolemic males; open circles indicate unaffected females; and filled circles indicate hyperglycerolemic females.

Glycerol is an important intermediate of glucose and lipid metabolism by virtue of its ability to support glycogenesis in various systems (Rognstad et al., *Biochem J.* 140(2):249–251 (1974)), as well as serving as a precursor of the synthesis of triglycerides (TG) and other glycerolipids (Catron and Lewis, *J. Biol Chem* 84:553–559 (1929); Shapiro, *J. Biol Chem* 108:373–387 (1935)). Administration of glycerol to healthy individuals has been demonstrated to result in increased serum glucose levels and/or gluconeogenesis (Sommer et al., *Arzneimittel Forschung* 43(7):744–747 (1993)), similar to the changes observed in various pathological situations such as type 2 diabetes mellitus (DM) (Guggenheim et al., *Ann Neurol.* 7:441–449 (1980); Frank et al., *Pharmacotherapy*, 1:147–160 (1980); Pelkonen et al., *Diabetologia* 3: 1–8 (1967)). It has also been shown that obese subjects have increased levels of plasma glycerol and increased glycerol turnover when compared with lean individuals (Jansson et al., *J. Clin Invest*. 89: 1610–1617 (1992); Jansson et al., *Am J. Physiol*. 258: E918–E922 (1990); Bjorntorp et al., *Acta Med Scand*. 179(2):221–227 (1966)). These observations indicated the potential importance of glycerol homeostasis in healthy individuals as well as in patients with abnormalities in glucose or lipid metabolism, who are at higher risk for DM or coronary artery disease.

The glycerol kinase (GK) enzyme is a candidate for this control since it mediates glycerol's entry into metabolic pathways. Genetic abnormalities involving the GK gene, which is located on chromosome Xp21.3 (Walker et al., *Hum Mol Genet* 2(2):107–114 (1993)), have been classified as either complex or isolated deficiencies (Rose et al., *J. Clin. Invest*. 978:61(1):163–170; McCabe et al., *Adv. Exp. Med. Biol*. 194:481–493 (1986); Blomquist et al., *Clin. Genet*. 50(5):375–379 (1996)). The complex GK deficiency (GKD) is a contiguous gene syndrome involving not only the GK locus, but also the Duchenne muscular dystrophy and/or the adrenal hypoplasia congenital gene loci (McCabe "Disorders of Glycerol Metabolism" *In the Metabolic Basis of inherited Disease*, $7^{th}$ Edn. (ed. Scriver C R et al.) McGraw-Hill, New York, pp. 945–961 (1995); Walker et al., *Hum. Mol. Genet*. 1(8):579–585 (1992); Davies et al., *Am. J. Med. Genet*. 29(3):557–564 (1988); Romero et al., *Neuromuscul. Disord*. 7(8):499–504 (1997)). In contrast, isolated GK deficiencies, which include juvenile and adult forms, result from either point mutations or small rearrangements within the GK gene (Walker et al., *Am. J. Hum. Genet*. 58(6):1205–1211 (1996); Sjarif et al., *J. Med. Genet*. 35(8):650–656 (1998)). The adult form is characterized by a phenotype of hyperglycerolemia, often detected along with pseudohypertriglyceridemia since the enzymatic measurement of TG is generally inferred from that of glycerol generated as a product of a lipolysis reaction. Apart from pseudohypertriglyceridemia, however, the clinical expression of the adult form of isolated GK deficiency is not well documented, mainly due to the small number of clinically and genetically heterogeneous families described in previous reports (Walker et al., *Am. J. Hum. Genet*. 58(6):1205–1211 (1996); Sjarif et al., *J. Med. Genet*. 35(8):650–656 (1998)). None of these studies was designed, nor had the power, to describe the metabolic phenotype in individuals having increased plasma glycerol levels in the fasting state.

Work described herein reports the findings of clinical and molecular genetic examinations of the largest group of individuals with severe hyperglycerolemia ever reported identified from a cohort of 1,056 unrelated French Canadians. This work provides evidence that fasting glycerolemia is a significant predictor of impaired glucose tolerance (IGT), and can be a potentially important genetic connection between plasma glycerol and glucose homeostasis.

It is likely that there are many different genes involved in the modulation of plasma glucose and lipid homeostasis. Among them are genes involved in the regulation of glycerol metabolism, since these pathways contribute directly or indirectly to cellular energy metabolism by providing mitochondria with substrate for oxidative phosphorylation (Sarate, *Science* 283(5407):1488–1493 (1999)). In this regard GK plays a pivotal role, since it mediates the entry of glycerol into metabolism, catalyzing the phosphorylation of glycerol by adenosine triphosphate (ATP) to yield glycerol 3-phosphate (G3P) and adenosine diphosphate (ADP) (Thomer et al., *J. Biol. Chem*. 248(1):3922–3932 (1973)).

Although glycerol is a well accepted indicator of lipolysis and a gluconeogenic precursor, the relationship between glycerol and glucose homeostasis is complex and not yet elucidated. One way to further this knowledge is to study cases of hyperglycerolemia, to establish the effect of glycerol levels in this extreme phenotype on the other metabolic pathways and then examine whether similar effects are observable in normoglycerolemic individuals.

Following this approach, the molecular and clinical characteristics of the largest sample of individuals with familial hyperglycerolemia ever reported were studied. Importantly, all families exhibiting this severe phenotype were identified through a systematic screening of fasting glycerol levels in a large number of individuals of French Canadian descent. The uniformity of this group of patients is clearly demonstrated by the observation that all affected individuals bear the same N288D mutation in the GK enzyme which is present on a haplotype common to all GKD families. The study of this rare deficiency in glycerol metabolism demonstrated that although all N288D carriers were hyperglycerolemic, significant inter-individual variations in glycerolemia were observed and these differences were found to explain an important part of the variance observed in glucose tolerance and abdominal obesity, a feature that has not been reported in previous studies on familial hyperglycerolemia.

In the subsequent examination of the large cohort of normoglycerolemic individuals it was determined that, in absence of the N288D mutation at the GK locus, fasting plasma glycerol concentrations have an important familial component in humans. This finding is notable since glycerol is usually only considered as an intermediate metabolite, its concentration being affected by multiple factors such as the degree of glycerol released by lipolysis, the rate of glyconeogenesis or glycogenolysis, obesity, starvation, exercise, the use of pharmaceutical preparations, and numerous pathological conditions. Despite this variety of environmental factors affecting glycerol concentrations, it was found that the heritability of fasting glycerolemia could be as high as 58% in humans, indicating an important genetic control. Furthermore, it was also found that plasma glycerol was a predictor of 2-hour glucose, independent of the variation in significant, well recognized, covariates of IGT or DM. This relationship of glycerol to 2-hour glucose was not linear across its distribution and a threshold in the relationship of glycerol of IGT was observed. Interestingly, in the absence of the N288D mutation, the threshold for glycerol concentrations was relatively low, at the level of the median of the studied population, so that even within what is considered as a "normal range" of glycerol levels, a moderate elevation in glycerol concentrations substantially increased the odds of finding patients with IGT. The possibility that the results of the OGTT can be predicted from the knowledge of the glycerolemia is clinically relevant, considering that measurement of plasma glycerol concentrations in the fasting state is a cheap and widely available analysis. Results of multivariate analyses clearly demonstrated that there are many other important IGT predictors, such as impaired fasting glucose and FFA concentrations. The association of glycerol with IGT, however, was independent of FFA and of fasting glucose concentrations. Furthermore, compared to FFA, plasma glycerol measurement in the fasting state is cheaper and is not affected by qualitative factors such as the degree of saturation.

Taken together, these results are most consistent with glycerol playing a regulatory role in the pathogenesis of IGT and DM. First, results from N288D carriers demonstrate that increased levels of glycerol is observable in the context of normal glucose tolerance. Indeed, even though the majority of men carrying a GK gene mutation met criteria of IGT or DM, some of them, exhibiting extremely elevated plasma glycerol concentrations (over 3.0 mmol/L), had normal 2-hour glucose values. Compared to N288D carriers with IGT, however, these individuals were younger and less obese. Furthermore, the majority of them also presented elevated fasting insulin concentration (above 30 mU/L) such that they are possibly at a higher risk of IGT.

Second, the essential position of glycerol in both glucose and glycerolipid metabolic pathways favors glycerol as a potential causal factor. Indeed, it is recognized that the contribution of glycerol to glucose production is directly correlated to its release as a consequence of lipolysis (Prentki et al., *J. Biol. Chem.*, 267(9):5802–5810 (1992)). However, under normal circumstances gluconeogenesis from glycerol accounts for only a small percentage of total glucose production, and an important proportion of glycerol metabolites is used for glycerolipid synthesis and not for glucose production. Notwithstanding these factors, variations in the glycerolemia among individuals with GK deficiency explained 68.9% of the variance in 2-hour glucose, and among non-carriers the prediction of 2-hour glucose by fasting glycerolemia was independent of fasting glucose concentration, suggesting that beyond glycerol-derived gluconeogenesis, glycerol is likely to have a regulatory role.

Thus, the current study of a large sample of unrelated individuals and of an homogeneous group of patients with a rare deficiency in glycerol metabolism indicate an important genetic connection between glycerol metabolism and the level of glucose tolerance, and supports the usefulness of measuring fasting plasma glycerol concentration in screening for the pre-diabetic phenotype.

The present invention also pertains to diagnostic assays and prognostic assays used for prognostic (predictive) purposes to thereby treat an individual prophylactically. Accordingly, one aspect of the present invention relates to diagnostic assays for determining protein and/or nucleic acid expression as well as activity of proteins of the invention, in the context of a biological sample (e.g., blood, serum, cells, tissue) to thereby determine whether an individual is afflicted with a disease or disorder, or is at risk of developing a disorder, e.g., type 2 diabetes mellitus, cardiovascular disease, hyperglycerolemia and/or impaired glucose tolerance, associated with aberrant expression or activity. The invention also provides for prognostic (or predictive) assays for determining whether an individual is at risk of developing a disorder associated with activity or expression of proteins or nucleic acids of the invention. Thus, such methods can predict or aid in the prediction of an individual's increased likelihood for developing a disorder, as well as assisting in the diagnosis of existing disorders.

For example, the invention provides methods of predicting or assisting in the prediction of diabetes mellitus, cardiovascular disease, hyperglycerolemia and/or impaired glucose tolerance in an individual, comprising the steps of obtaining a biological sample from an individual and assessing glycerol levels in said sample, wherein increased levels of glycerol in said sample as compared with a control sample, e.g., from a normal individual, is predictive of diabetes mellitus, cardiovascular disease, hyperglycerolemia and/or impaired glucose tolerance in the individual. In a preferred embodiment, the diabetes mellitus is type 2 diabetes mellitus. In one embodiment, increased glycerol levels are greater than about 0.08 mmol/L. Alternatively, one could assess levels of GK gene expression or levels of active GK protein present in the sample. Increased levels as compared with a suitable control are indicative of increased likelihood of diabetes mellitus and/or IGT in the individual. In one embodiment, the biological sample is a blood sample, such as a fasting blood sample. In a preferred embodiment, the glycerol levels which are assessed are plasma glycerol levels.

An exemplary method for detecting the presence or absence of proteins or nucleic acids of the invention in a biological sample involves obtaining a biological sample from a test subject and contacting the biological sample with a compound or an agent capable of detecting the protein (e.g., the glycerol protein or the GK protein), or nucleic acid (e.g., mRNA, genomic DNA) that encodes the GK protein, such that the presence of the protein or nucleic acid is detected in the biological sample. A preferred agent for detecting mRNA or genomic DNA is a labeled nucleic acid probe capable of hybridizing to mRNA or genomic DNA sequences described herein. The nucleic acid probe can be, for example, a full-length nucleic acid, or a portion thereof, such as an oligonucleotide of at least 15, 30, 50, 100, 250 or 500 nucleotides in length and sufficient to specifically hybridize under stringent conditions to appropriate mRNA or genomic DNA. Other suitable probes for use in the diagnostic assays of the invention are described herein.

In another embodiment, the invention provides a method of predicting or assisting in the prediction of diabetes mellitus or impaired glucose tolerance in an individual, comprising the steps of obtaining a nucleic acid sample from an individual and determining the nucleotide present at nucleotide position 29 of exon 10, wherein presence of a guanine at said position is predictive of diabetes mellitus or impaired glucose tolerance in the individual as compared with an appropriate control, e.g., an individual having an adenosine at said position.

In one embodiment, the agent for detecting proteins of the invention is an antibody capable of binding to the protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. In a preferred embodiment, the antibody is able to distinguish between complete or nearly complete proteins and truncated versions of the same protein.

The term "biological sample" is intended to include tissues, calls and biological fluids isolated from a subject, as well as tissues, cells and fluids present within a subject. For example, the sample can be obtained from a tissue selected from the group consisting of: brain tissue, CNS, lung, fetal lung, testis, lymphocytes, adipose, fibroblasts, skeletal muscle, pancreas, uterus, kidney, tonsil, embryo and isolated cells thereof. That is, the detection method of the invention can be used to detect mRNA, protein, or genomic DNA of the invention in a biological sample in vitro as well as in vivo. For example, in vitro techniques for detection of mRNA include Northern hybridizations and in situ hybridizations. In vitro techniques for detection of protein include enzyme linked immunosorbent assays (ELISAs), Western blots, immunoprecipitations and immunofluorescence. In vitro techniques for detection of genomic DNA include Southern hybridizations. Furthermore, in vivo techniques for detection of protein include introducing into a subject a labeled anti-protein antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample obtained by conventional means from a subject. A nucleic acid sample is a sample, e.g., a biological sample, which contains nucleic acid molecules.

The invention also encompasses kits for detecting the presence of proteins or nucleic acid molecules of the invention in a biological sample. For example, the kit can comprise a labeled compound or agent capable of detecting protein or mRNA in a biological sample; means for determining the amount of in the sample; and means for comparing the amount of in the sample with a standard. The compound or agent can be packaged in a suitable container. The kit can further comprise instructions for using the kit to detect protein or nucleic acid.

In certain embodiments as described herein, it is valuable to determine the genotype of an individual, particularly where a specific allelic form of the GK gene has now been associated with disease. For example, it will be valuable for purposes of diagnosis to determine which allelic form of the N288D mutation an individual has with respect to cardiovascular disease, hyperglycerolemia, IGT or DM diagnosis.

Detection of the alteration can involve the use of a probe/primer in a polymerase chain reaction (PCR) (see, e.g., U.S. Pat. Nos. 4,683,195 and 4,683,202), such as an anchor PCR or RACE PCR, or, alternatively, in a ligation chain reaction (LCR) (see, e.g., Landegran et al. (1988) *Science*, 241:1077–1080; and Nakazawa et al. (1994) *PNAS*, 91:360–364), the latter of which can be particularly useful for detecting point mutations (see Abravaya et al. (1995) *Nucleic Acids Res.*, 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to the gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. In one embodiment, allele-specific primers are utilized.

Alternative amplification methods include: self sustained sequence replication (Guatelli, J. C. et al. (1990) *Proc. Natl. Acad. Sci. USA*, 87:1874–1878), transcriptional amplification system (Kwoh, D. Y. et al., (1989) *Proc. Natl. Acad. Sci. USA*, 86:1173–1177), Q-Beta Replicase (Lizardi, P. M. et al., (1988) *Bio/Technology*, 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a given gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicate mutations in the sample DNA. Moreover, the use of sequence specific ribozymes (see, for sample, U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotide probes (Cronin, M. T. et al. (1996) *Human Mutation*, 7:244–255; Kozal, M. J. et al. (1996) *Nature Medicine*, 2:753–759). For example, genetic mutations can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the gene and detect mutations by comparing the sequence of the gene from the sample with the corresponding wild-type (control) gene sequence. Examples of sequencing reactions include those based on techniques developed by Maxim and Gilbert ((1997) *PNAS*, 74:560) or Sanger ((1977) *PNAS*, 74:5463). It is also contemplated that any of a variety of automated sequencing procedures can be utilized when performing the diagnostic assays ((1995) *Biotechniques*, 19:448), including sequencing by mass spectrometry (see, e.g., PCT International Publication No. WO 94/16101; Cohen et al. (1996) *Adv. Chromatogr.*, 36:127–162; and Griffin et al. (1993) *Appl. Biochem. Biotechnol.*, 38: 147–159).

In other embodiments, alterations in electrophoretic mobility will be used to identify mutations in genes. For example, single strand conformation polymorphism (SSCP) may be used to detect differences in electrophoretic mobility between mutant and wild type nucleic acids (Orita et al. (1989) *Proc. Natl. Acad. Sci. USA*, 86:2766, see also Cotton (1993) *Mutat Res*, 285:125–144; and Hayashi (1992) *Genet Anal. Tech. Appl.*, 9:73–79). Single-stranded DNA fragments of sample and control nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.*, 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature*, 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.*, 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature*, 324:163); Saiki et al. (1989) *Proc. Natl. Acad. Sci. USA*, 86:6320). Such allele-specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.*, 17:2437–2448) or at the extreme 3' end of one primer where, under appropriate conditions, mismatch can prevent, or reduce polymerase extension (Prossner (1993) *Tibtech*, 11:238). In addition it may be desirable to introduce a novel restriction site in the region of the mutation to create cleavage-based detection (Gasparini et al. (1992) *Mol. Cell Probes*, 6:1). It is anticipated that in certain embodiments amplification may also be performed using Taq ligase for amplification (Barany (1991) *Proc. Natl. Acad. Sci. USA*, 88:189). In such cases, ligation will occur only if there is a perfect match at the 3' end of the 5' sequence making it possible to detect the presence of a known mutation at a specific site by looking for the presence or absence of amplification. Single base extension (SBE) and SBE fluorescence resonance energy transfer (SBE-FRET) can also be used to identify the specific nucleotide which occupies a given position in a nucleic acid molecule.

The methods described herein may be performed, for example, by utilizing pre-packaged diagnostic kits comprising at least one probe nucleic acid molecule or antibody reagent described herein, which may be conveniently used, e.g., in clinical settings to diagnose patients exhibiting symptoms or family history of a disease or illness involving a gene of the present invention. Any cell type or tissue in which the gene is expressed may be utilized in the prognostic assays described herein.

The invention also relates to isolated nucleic acid molecules comprising SEQ ID NOS: 1–4. SEQ ID NOS: referred to herein are as follows. SEQ ID NO: 1 refers to the nucleic acid sequence of the GK gene having a polymorphic site at nucleotide position 13 of exon 3 as shown in FIG. 6. SEQ ID NO: 2 refers to the nucleic acid sequence of the GK gene having a polymorphic site at nucleotide position 17 of intron 8 as shown in FIG. 6. SEQ ID NO: 3 refers to the nucleic acid sequence of the GK gene having a polymorphic site at nucleotide position 29 of exon 10 as shown in FIG. 6. SEQ ID NO: 4 refers to the nucleic acid sequence of the GK gene having polymorphic site at nucleotide position 22 of intron 12 as shown in FIG. 6. In one embodiment, SEQ ID NOS: 1–4 comprise the reference (first) nucleotide at the polymorphic site. In another embodiment, SEQ ID NOS: 1–4 comprise the alternate (second) nucleotide at the polymorphic site. SEQ ID NO: 5 refers to the complete coding nucleic acid sequence of the GK gene, particularly as shown in FIGS. 7A–7D.

As appropriate, the isolated nucleic acid molecules of the present invention can be RNA, for example, mRNA, or DNA, such as cDNA and genomic DNA. DNA molecules can be double-stranded or single-stranded; single stranded RNA or DNA can be either the coding, or sense, strand or the non-coding, or antisense, strand. The nucleic acid molecule can include all or a portion of the coding sequence of a gene and can further comprise additional non-coding sequences such as introns and non-coding 3' and 5' sequences (including regulatory sequences, for example). Additionally, the nucleic acid molecule can be fused to a marker sequence, for example, a sequence that encodes a polypeptide to assist in isolation or purification of the polypeptide. Such sequences include, but are not limited to, those which encode a glutathione-S-transferase (GST) fusion protein and those which encode a hemaglutin A (HA) polypeptide marker from influenza. As used herein, "isolated" is intended to mean that the isolated item is not in the form or environment in which it exists in nature. For example, an "isolated" nucleic acid molecule, as used herein, is one that is separated from nucleic acid which normally flanks the nucleic acid molecule in nature. With regard to genomic DNA, the term "isolated" refers to nucleic acid molecules which are separated from the chromosome with which the genomic DNA is naturally associated. For example, the isolated nucleic acid molecule can contain less than about 5 kb, 4 kb, 3 kb, 2 kb, 1 kb, 0.5 kb or 0.1 kb of nucleotides which flank the nucleic acid molecule in the genomic DNA of the cell from which the nucleic acid is derived.

Moreover, an isolated nucleic acid of the invention, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated. In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

Further, recombinant DNA contained in a vector is included in the definition of "isolated" as used herein. Also, isolated nucleic acid molecules include recombinant DNA molecules in heterologous host cells, as well as partially or substantially purified DNA molecules in solution. "Isolated" nucleic acid molecules also encompass in vivo and in vitro RNA transcripts of the DNA molecules of the present invention produced in a heterologous host cell. The present invention also provides isolated nucleic acids that contain a fragment or portion of SEQ ID NOS: 1–4 described herein and the complements of SEQ ID NOS: 1–4. Preferred fragments comprises a polymorphic site, and in a preferred embodiment the polymorphic site is occupied by the alternate nucleotide. The nucleic acid fragments of the invention are at least about 15, preferably at least about 18, 20, 23 or 25 consecutive nucleotides, and can be 30, 40, 50, 100, 200 or more nucleotides in length. Longer fragments, for example, 30 or more nucleotides in length, which encode antigenic proteins or polypeptides described herein are useful.

In a related aspect, the nucleic acid fragments of the invention are used as probes or primers in assays such as those described herein. "Probes" are oligonucleotides that hybridize in a base-specific manner to a complementary strand of nucleic acid. Such probes include polypeptide nucleic acids, as described in Nielsen et al., *Science*, 254, 1497–1500 (1991). Typically, a probe comprises a region of nucleotide sequence that hybridizes under highly stringent conditions to at least about 15, typically about 20–25, and more typically about 40,.50 or 75 consecutive nucleotides of a nucleic acid molecule of the invention. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The nucleic acid molecules of the invention such as those described above can be identified and isolated using standard molecular biology techniques and the sequence information provided herein. For example, nucleic acid molecules can be amplified and isolated by the polymerase chain reaction using synthetic oligonucleotide primers designed based on one or more of the sequences provided herein and the complements thereof. See generally *PCR Technology: Principles and Applications for DNA Amplification* (ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.*, 19:4967 (1991); Eckert et al., *PCR Methods and Applications*, 1:17 (1991); PCR (eds. McPherson et al., IRL Press, Oxford); and U.S. Pat. No. 4,683,202. The nucleic acid molecules can be amplified using cDNA, mRNA or genomic DNA as a template, cloned into an appropriate vector and characterized by DNA sequence analysis.

Other suitable amplification methods include the ligase chain reaction (LCR) (see Wu and Wallace, *Genomics*, 4:560 (1989), Landegren et al., *Science*, 241:1077 (1988), transcription amplification (Kwoh et al., *Proc. Natl. Acad. Sci. USA*, 86:1173 (1989)), and self-sustained sequence replication (Guatelli et al., *Proc. Nat. Acad. Sci. USA*, 87:1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be radiolabelled and used as a probe for screening a cDNA library derived from mRNA in zap express, ZIPLOX or other suitable vector. Corresponding clones can be isolated, DNA can obtained following in vivo excision, and the cloned insert can be sequenced in either or both orientations by art recognized methods to identify the correct reading frame encoding a protein of the appropriate molecular weight. For example, the direct analysis of the nucleotide sequence of nucleic acid molecules of the present invention can be accomplished using well-known methods that are commercially available. See, for example, Sambrook et al., *Molecular Cloning, A Laboratory Manual* (2nd Ed., CSHP, New York 1989); Zyskind et al., *Recombinant DNA Laboratory Manual*, (Acad. Press, 1988)). Using these or similar methods, the protein(s) and the DNA encoding the protein can be isolated, sequenced and further characterized.

Antisense nucleic acids of the invention can be designed using the nucleotide sequences described herein, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

In general, the isolated nucleic acid sequences can be used as molecular weight markers on Southern gels, and as chromosome markers which are labeled to map related gene positions. The nucleic acid sequences can also be used to compare with endogenous DNA sequences in patients to identify genetic disorders, and as probes, such as to hybridize and discover related DNA sequences or to subtract out known sequences from a sample. The nucleic acid sequences can further be used to derive primers for genetic fingerprinting, to raise anti-protein antibodies using DNA immunization techniques, and as an antigen to raise anti-DNA antibodies or elicit immune responses. Additionally, the nucleotide sequences of the invention can be used identify and express recombinant proteins for analysis, characterization or therapeutic use, or as markers for tissues in which the corresponding protein is expressed, either constitutively, during tissue differentiation, or in diseased states.

The invention also relates to constructs which comprise a vector into which a sequence of the invention has been inserted in a sense or antisense orientation. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses) that serve equivalent functions.

Preferred recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc.

The expression vectors of the invention can be introduced into host cells to thereby produce proteins or peptides, including fusion proteins or peptides, encoded by nucleic acids as described herein. The recombinant expression vectors of the invention can be designed for expression of a polypeptide of the invention in prokaryotic or eukaryotic cells, e.g., bacterial cells such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the tern as used herein.

A host cell can be any prokaryotic or eukaryotic cell. For example, a nucleic acid of the invention can be expressed in bacterial cells (e.g., *E. coli*), insect cells, yeast or mammalian cells (such as Chinese hamster ovary cells (CHO) or COS cells). Other suitable host cells are known to those skilled in the art. For example, suitable cells can be derived from tissues such as adipocytes, lymphoblasts and fibroblasts.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et a. (supra), and other laboratory manuals.

A host cell of the invention, such as a prokaryotic or eukaryotic host cell in culture, can be used to produce (i.e., express) a polypeptide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a nucleic acid of the invention have been introduced. Such host cells can then be used to create non-human transgenic animals in which exogenous nucleotide sequences have been introduced into their genome or homologous recombinant animals in which endogenous nucleotide sequences have been altered. Such animals are useful for studying the function and/or activity of the nucleotide sequence and polypeptide encoded by the sequence and for identifying and/or evaluating modulators of their activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid of the invention into the male pronuclei of a fertilized oocyte, e.g., by microinjection, retroviral infection, and allowing the oocyte to develop in a pseudopregnant female foster animal. The sequence can be introduced as a transgene into the genome of a non-human animal. Intronic sequences and polyadenylation signals can also be included in the transgene to increase the efficiency of expression of the transgene. A tissue-specific regulatory sequence(s) can be operably linked to the transgene to direct expression of a polypeptide in particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA in tissues or cells of the animals. A transgenic founder animal can then be used to breed additional animals carrying the transgene. Moreover, transgenic animals carrying a transgene encoding the transgene can further be bred to other transgenic animals carrying other transgenes.

The host cells of the invention can also be used as an in vitro model to assess the ability of agents to act as agonists of glycerol kinase or the glycerol kinase-mediated pathway of glycerol metabolism. For example, a suitable host cell can be transfected with a nucleic acid molecule encoding SEQ ID NO: 3 comprising the alternate nucleotide at the polymorphic site, which results in a defective glycerol metabolism pathway. Such cells can then be contacted with one or more agents to test their ability to overcome this defect, i.e., to act as agonists of glycerol kinase. As used herein, an agonist is an agent which increases or enhances the activity or effect of glycerol kinase. For example, an agent which mediates phosphorylation of glycerol by adenosine triphosphate (ATP) to yield glycerol 3-phosphate (G3P) and adenosine diphosphate (ADP) can be an agonist of glycerol kinase. The ability of an agent to act as an agonist can be tested, for example, using the level of a molecule downstream of glycerol kinase in the glycerol metabolic path as an indicator. For example, one could assess the agent's ability to increase G3P or ADP production relative to a suitable control, e.g., a cell which has not been contacted with the agent.

The present invention also provides isolated polypeptides and variants and fragments thereof that are encoded by the nucleic acid molecules of the invention. For example, as described above, the nucleotide sequences can be used to design primers to clone and express cDNAs encoding the polypeptides of the invention. In one embodiment, a polypeptide of the invention has an amino acid sequence encoded by SEQ ID NO: 5. In another embodiment, the polypeptide has the amino acid sequence of the wild type GK protein (e.g., comprising SEQ ID NO: 6) except that the protein comprises an aspartate as the tenth amino acid encoded by exon 10.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be "isolated" or "purified."

The polypeptides of the invention can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity. In one embodiment, the language "substantially free of cellular material" includes preparations of the polypeptide having less than about 30% (by dry weight) other proteins (i.e., contaminating protein), less than about 20% other proteins, less than about 10% other proteins, or less than about 5% other proteins.

When a polypeptide is recombinantly produced, it can also be substantially free of culture medium, i.e., culture medium represents less than about 20%, less than about 10%, or less than about 5% of the volume of the protein preparation. The language "substantially free of chemical precursors or other chemicals" includes preparations of the polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

The invention also includes polypeptide fragments or portions of the polypeptides of the invention, as well as fragments of the variants of the polypeptides described herein. As used herein, a fragment comprises at least 6 contiguous amino acids. Useful fragments include those that retain one or more of the biological activities of the polypeptide as well as fragments that can be used as an immunogen to generate polypeptide specific antibodies. Particularly preferred polypeptides are those which comprise an alternate amino acid encoded by a polymorphic nucleic acid.

Biologically active fragments (peptides which are, for example, 6, 9, 12, 15, 20, 30, 35, 36, 37, 38, 39, 40, 50, 100 or more amino acids in length) can comprise a domain, segment, or motif that has been identified by analysis of the polypeptide sequence using well-known methods, e.g., signal peptides, extracellular domains, one or more transmembrane segments or loops, ligand binding regions, zinc finger domains, DNA binding domains, acylation sites, glycosylation sites, or phosphorylation sites. Preferred fragments or portions comprise an amino acid encoded by a codon containing a polymorphic site, e.g., as shown in FIGS. 6 and 7A–7D. In a preferred embodiment, the amino acid is the alternate amino acid.

The invention also provides fragments with immunogenic properties. These contain an epitope-bearing portion of the polypeptides and variants of the invention. These epitope-bearing peptides are useful to raise antibodies that bind specifically to a polypeptide or region or fragment. These peptides can contain at least 6, 7, 8, 9, 12, at least 14, or between at least about 15 to about 30 amino acids. The epitope-bearing peptide and polypeptides may be produced by any conventional means (Houghten, R. A., *Proc. Natl. Acad. Sci. USA*, 82:5131–5135 (1985)). Simultaneous multiple peptide synthesis is described in U.S. Pat. No. 4,631, 211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

The invention thus provides chimeric or fusion proteins. These comprise a polypeptide of the invention operatively linked to a heterologous protein having an amino acid sequence not substantially homologous to the polypeptide. "Operatively linked" indicates that the polypeptide protein and the heterologous protein are fused in-frame. The heterologous protein can be fused to the N-terminus or C-terminus of the polypeptide. In one embodiment the fusion protein does not affect function of the polypeptide per se. For example, the fusion protein can be a GST-fusion protein in which the polypeptide sequences are fused to the C-terminus of the GST sequences. The isolated polypeptide can be purified from cells that naturally express it, such as from mammary epithelium, purified from cells that have been altered to express it (recombinant), or synthesized using known protein synthesis methods.

In one embodiment, the protein is produced by recombinant DNA techniques. For example, a nucleic acid molecule encoding the polypeptide is cloned into an expression vector, the expression vector introduced into a host cell and the protein expressed in the host cell. The protein can then be isolated from the cells by an appropriate purification scheme using standard protein purification techniques.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

In general, polypeptides or proteins of the present invention can be used as a molecular weight marker on SDS-PAGE gels or on molecular sieve gel filtration columns using art-recognized methods. The polypeptides of the present invention can be used to raise antibodies or to elicit an immune response. The polypeptides can also be used as a reagent, e.g., a labeled reagent, in assays to quantitatively determine levels of the protein or a molecule to which it binds (e.g., a receptor or a ligand) in biological fluids. The polypeptides can also be used as markers for tissues in which the corresponding protein is preferentially expressed, either constitutively, during tissue differentiation, or in a diseased state. The polypeptides can be used to isolate a corresponding binding partner, e.g., receptor or ligand, such as, for example, in an interaction trap assay, and to screen for peptide or small molecule antagonists or agonists of the binding interaction.

In another aspect, the invention provides antibodies to the polypeptides and polypeptide fragments of the invention. The term "antibody" as used herein refers to immunoglobulin molecules and immunologically active portions of immunoglobulin molecules, i.e., molecules that contain an antigen binding site that specifically binds an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind to a polypeptide of the invention; such antibodies can be made using methods known in the art. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it inmmunoreacts.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science*, 240:1041–1043; Liu et al. (1987) *Proc. Natl. Acad. Sci. USA*, 84:3439–3443; Liu et al. (1987) *J. Immunol.*, 139:3521–3526; Sun et al. (1987) *Proc. Natl. Acad. Sci. USA*, 84:214–218; Nishimura et al. (1987) *Canc. Res.*, 47:999–1005; Wood et al. (1985) *Nature*, 314:446–449; and Shaw et al. (1988) *J. Natl. Cancer Inst.*, 80:1553–1559); Morrison (1985) *Science*, 229:1202–1207; Oi et al. (1986) *Bio/Techniques*, 4:214; U.S. Pat. No. 5,225,539; Jones et al. (1986) *Nature*, 321:552–525; Verhoeyan et al. (1988) *Science*, 239:1534; and Beidler et al. (1988) *J. Immunol.*, 141:4053–4060.

In general, antibodies of the invention (e.g., a monoclonal antibody) can be used to isolate a polypeptide of the invention by standard techniques, such as affinity chromatography or immunoprecipitation. A polypeptide specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen, Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, (β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The invention will now be described by the following non-limiting examples. The teachings of all references cited herein are incorporated herein by reference in their entirety.

EXAMPLES

Methods

Subjects:

All individuals appearing in the various pedigrees included in this study were derived from a large cohort of 1,056 unrelated individuals (the probands) of French Canadian descent aged ≧18 years who presented at the Chicoutimi Hospital Lipid Clinic for lipid screening and who had hypertriglyceridemia or a positive family history of hypertriglyceridemia, defined as a fasting triglyceride concentration above the 50$^{th}$ age- and sex-specific percentile according to the Lipid Research Clinic Program (LRCP)

criteria (Gaudet et al., *Circulation* 97(9):871–877 (1998)). Patients taking drugs known to affect plasma glycerol concentrations (McCabe, "Disorders of Glycerol Metabolism" in *The Metabolic Basis of Inherited Disease*, 7$^{th}$ Edn. (ed. Scriver C R et al.) McGraw-Hill, New York, pp. 945–961 (1995), as well as individuals presenting a medical condition potentially associated with secondary hyperglycerolemia, such as previously diagnosed DM, thyroid disorders or renal insufficiency, were excluded.

Linkage to the Xp21.3 Locus:

A total of twelve microsatellite markers in the region of the GK gene were genotyped in the five families with hyperglycerolemia. These markers were: DXS989, DXS8039, DXS1214, DXS1036, DXS1067, DXS1219, DXS997, DXS8090, DXS8025, DXS8113, DXS8042, and DXS8012. Genotypes for these markers were obtained by polymerase chain reaction (PCR) using fluorescently-labeled primers. The fluorescent genotyping gels were analyzed in an automat ed system developed at the Whitehead Institute/MIT Center for Genome Research as previously described (Kruglyak et al., *Am. J. Hum Genet.* 58:1347–1363 (1996)).

Multipoint parametric linkage analysis of genotype data was performed using the GENEHUNTER software package (Rioux et al., *Am. J. Hum. Genet.* 63(4):1086–1094 (1998)). Marker order and genetic distances used in the analysis were based on an integration of the published genetic map (CEPH-Genethon Database) and radiation hybrid mapping information obtained using the Genebridge 4 hybrid panel (Rioux et al., *Am J. Hum Genet.* 63(4):1086–1094 (1998)). The GK disease-allele frequency was estimated at 0.001 (McCabe et al., *Am J Hem Genet.* 51(6):1277–1285 (1992)), while values for male penetrance of 0.999, and female penetrance of 0.900 and 0.999 (heterozygotes and homozygotes, respectively) were used.

Genomic Structure of the GK Gene:

Genomic sequences were sought for the intronic regions surrounding exons 9, 10, 11, and 17. PAC clone RPCI-5.931_C_24 containing exons 9, 10, and 11 was identified using primer pairs GK08 and GK12, and PAC clone RPCI-5.1150 containing exon 17 was identified using primers GK17F and GK17R. All details regarding primer sequences and annealing temperatures are available on the Chicoutimi Hospital Lipid Research Group and Whitehead Institute/MIT Center for Genome Research GK websites. Direct sequencing of introns 9 and 10 from clone RPCI-5.931_C_24 using specific exonic primers (GK9F, GK10F, and GK10R), was carried out with the Big Dye terminator cycle sequencing kit (PE Applied BioSystems, Foster City, Calif.), and run on AB1377 automated sequencers.

To obtain the genomic sequence from intron 17, a single colony of clone RPCI-5.1150_E_8 was diluted in 100 μl of water and used as template for PCR amplification. An amplicon covering exon 17 through exon 18 was obtained with primers GK17_F AND GK18_R (FIG. 2), using the Platinum Taq High Fidelity (Life Technologies, Rockville, Md.). The PCR product was purified using the solid phase reversible immobilization (SPRI) method (Hawkins et al., *Nucleic Acids Research* 22:4543–4544 (1994)), and then sequenced using the DYEnamic Energy Transfer primer kit (Amersham Pharmnacia Biotech Ltd., Cleveland, Ohio).

GK Mutation Screening:

The screening for mutations in the GK gene was first performed by resequencing this gene in 9 affected individuals, 4 obligate carriers, and 3 unaffected relatives from the five families described above. Intronic primers used were previously published (Sargent et al., *Hum Mol Genet.* 3(8):1317–1324 (1994)) or designated from the sequence determined in the present study using the Primer 3.0 software available on the Whitehead Institute/MIT Center for Genome Research server. Sequencing reactions and gels were prepared and analyzed on ABI377 sequencers. Regions in which sequence polymorphisms were discovered were resequenced in 9 other affected individuals, 10 obligate carriers, and unaffected relatives from the GK families.

Plasma Glycerol and Other Biological Measurements:

Blood samples were drawn at rest after a 12-hour overnight fast from an antecubital vein into tubes containing EDTA. Specimens were centrifuged within one hour, and the separated plasma frozen (–80° C.) until analysis. TG and free fatty acid (FFA) levels were measured using enzymatic assays (McNamara et al., *Clin Chim Acta* 166:1–8 (1987)). Plasma glycerol concentrations were measures using an analyzer (Technicon RA-500 Bayer Corporation, Tarrytown, N.Y.) and enzymatic reagents obtained from Randox (Randox Laboratories Ltd., Crumlin, UK). Glycerol measurements were calibrated with reference standards purchased from Sigma (Sigma Diagnostics, St. Louis, USA). Waist and hip circumferences (Standardization of Anthropometric Measurements. In: Lohaman V., et al., eds, The Airle (VA) Concensus Conference *Human Kinetics* 1988:39–80), body weight, height and BMI were recorded. The % body fat was estimated by bio-electrical impedance (Baumgartner et al., *Exerc Sport Sci Rev.* 18:193–224 (1990)). Family history of DM was defined as the presence of a confirmed diagnosis in a first degree relative. An oral glucose tolerance test (OGTT) was performed in the original cohort of 1,056 individuals and in the families of the five GK carrier probands using a 75 g glucose load as previously described (Report of the Expert Committee on the Diagnosis and Classification of Diabetes Mellitus, Richterich et al., *Diabetes Care* 20:1183–1197 (1997)), and plasma glucose concentration was enzymatically measured (Richterich et al., *Schweiz Med Wochenschr* 101(17):615–618 (1971)). IGT and DM were defined according to the World Health Organization. Fasting insulinemia was measured by RIA with polyethylene glycol separation. (Desbuquois et al., *J. Clin Endocrinol Metab* 33(5):732–738 (1971)).

Calculation of Familial Resemblance of Fasting Glycerol Concentration:

After having excluded families of subjects bearing the N288D mutation, calculation of familial resemblance of plasma glycerol concentrations in the fasting state was performed for a total of 653 individuals arising from the nuclear families of 174 randomly selected patients of the initial cohort representing all deciles of fasting glycerol values. Before analyses, glycerol data were adjusted for age suing sex-specific regressions, and the residuals from these regressions were standardized to a mean of zero and standard deviation of 1. The standardized residuals were used to assess the degree of familial resemblance by computing the intraclass correlations (r) as previously described (Perusse et al., *Arterioscler Thromb Vasc Biol.* 17(11):3270–3277 (1997)). This correlation was calculated by computing the ratio of the between family variance over the sum of the within- and between-family variances estimated using a random effect model of analysis of variance (ANOVA) (Bogardus et al., *N Engl J. Med* 315(2):96–100 (1986)).

Statistical Analysis:

Group differences for plasma glycerol concentrations and other continuous variables were examined by the Student's unpaired two-tailed t-test. Linear regression models were used to assess the relationship between the dependent variables (2-hour glucose following a 75 g oral absorption or correlates of body fat accumulation) and fasting glycerolemia. To specifically study the ability of glycerol to predict IGT or DM (defined as 2-hour glucose ≧7.8 mmol/L following a 75 g oral glucose load), multiple logistic regression models were constructed. In a multiple regression analysis estimates were provided after adjustment for significant covariates such as age, gender, the BMI, fasting glucose, insulin, FFA and TG concentrations. The distribution of plasma TG, insulin, and glycerol levels was normalized by log-10 transformation.

Results

Figure 1B:
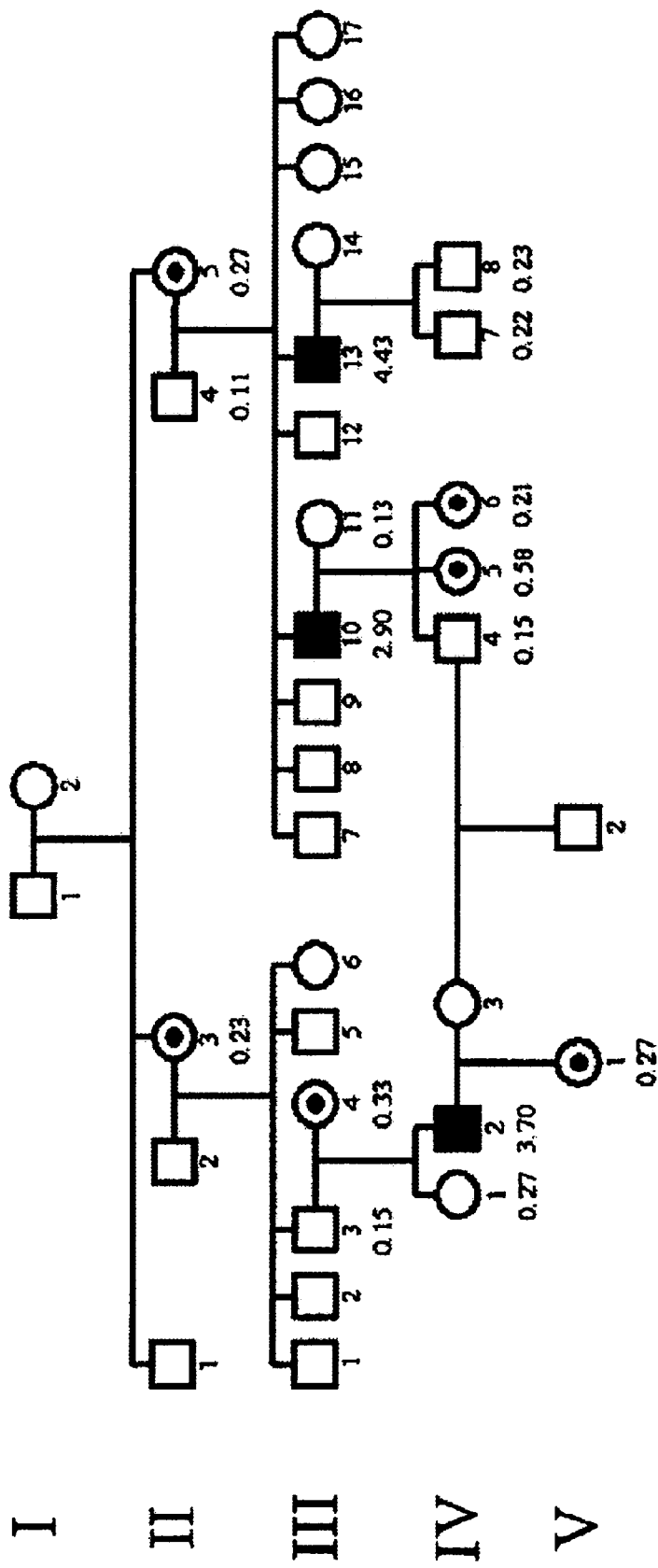
Figure 1C:
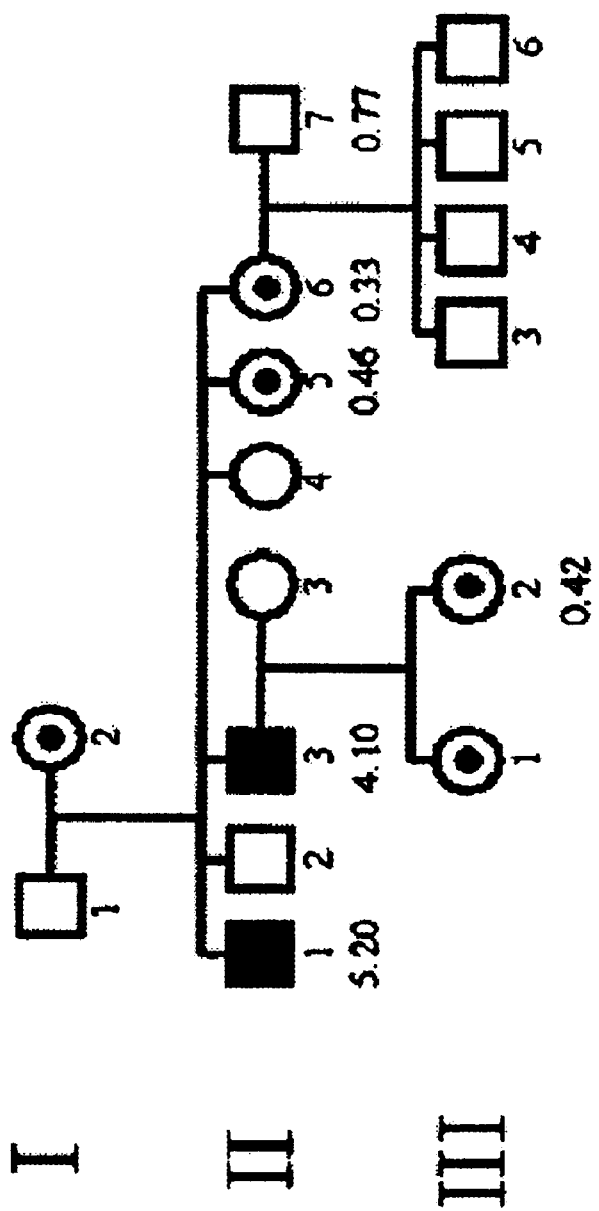

Severe Hyperglycerolemia Families:

From the sample of 1,056 subjects screened, five male individuals presented with plasma glycerol values above 2.0 mmol/L. Screening of their families identified a total of 18 males demonstrating extremely elevated plasma glycerol levels (range 2.9–6.2 mmol/L). Based on the pedigree data shown in FIG. 1, it was clear that the severe hyperglycerolemia phenotype segregated as a simple X-linked trait. In addition, 14 obligate female carriers were found to be dysglycerolemic, presenting intermediate plasma glycerol levels ranging from 0.01 to 0.82 mmol/L, whereas all other family members showed plasma glycerol concentrations below 0.2 mmol/L.

Linkage to Xp21.2:

12 microsatellite markers from Xp21.3 were genotyped among the affected pedigrees. Multipoint parametric linkage analysis of the genotype data resulted in a peak LOD score of 3.46 centered at marker DXS8039. As all families originate from a population with a proven founder effect (Perusse et al., *Arterioscler Thromb Vasc Biol* 17(11):3270–3277 (1997)), a common disease haplotype was looked for. A six-marker haplotype consisting of markers DXS8039, DXS1214, DXS1036, DXS1067, DXS1219 and DXS997 (alleles 151, 21, 145, 222, 230, 107) was observed in all families. This haplotype extended over a region of 5.5 cM.

Genomic Structure of GK Gene:

Intronic sequences surrounding exons 9, 10, 11, and 17, were persued in order to design primers to complete the set of previously reported oligonucleotides (Sargent et al., *Hum Mol Genet* 3(8):1317–1324 (1994)). In addition, when the sequence obtained for intron 10 was aligned with the published cDNA sequence, it was discovered that the splice junctions had been incorrectly defined, such that the last 12 bases of exon 10 were in fact encoded by exon 11.

Figure 2:
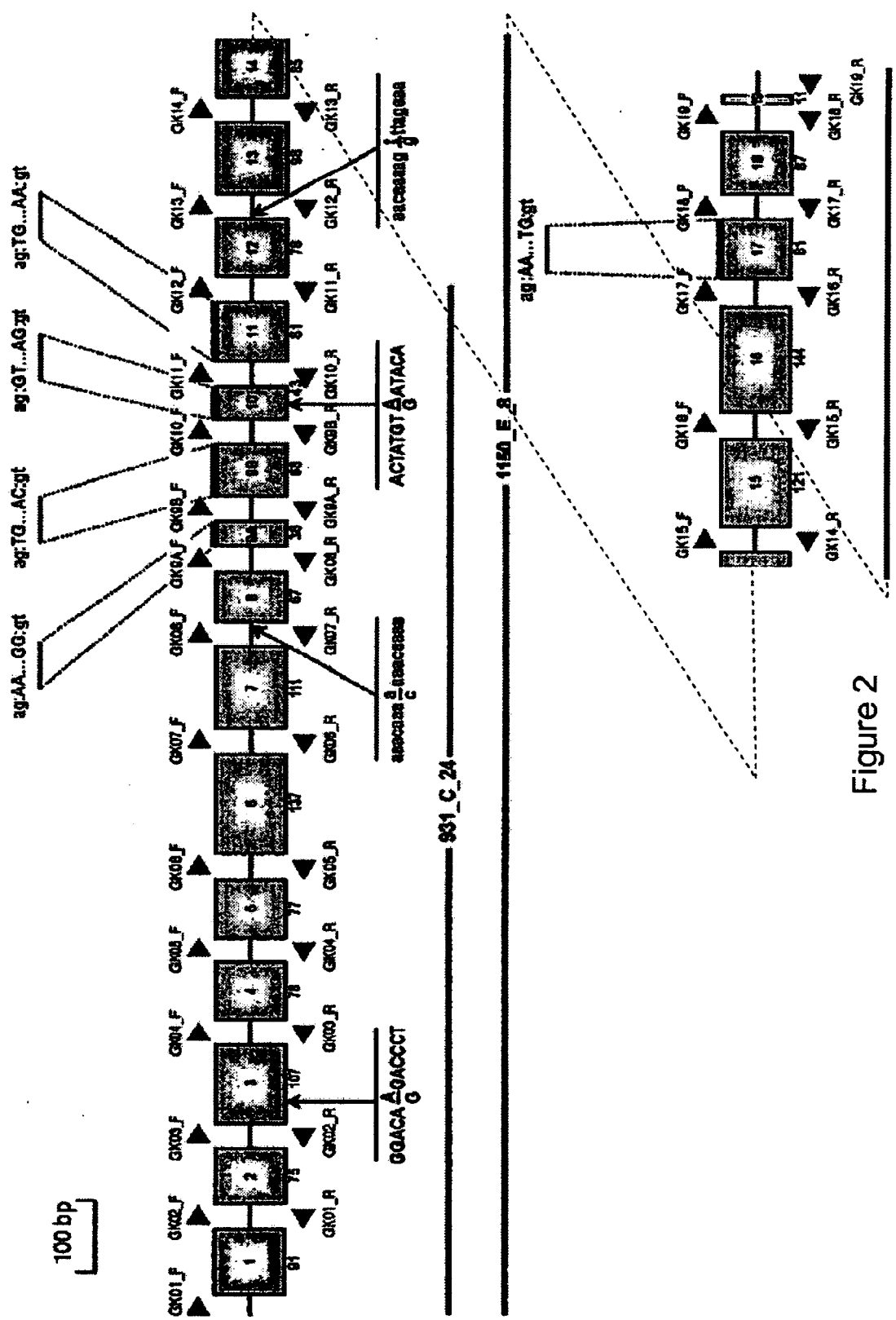
FIG. 2 shows the exonic structure of the Xp GK gene and location of sequence polymorphisms. The first PAC clone, RPCI-5.931_C_24, containing exons 1 to 12 was used as sequencing template for exons 9, 10 and 11. An insert of 394 base pairs (bp) was found after the 36th nucleotide of exon 9, suggesting that the originally described exon actually consists of two exons (9A and 9B). These exons are 36 and 68 bases in length, respectively, and the corresponding intron-exon boundaries have the expected consensus splice site sequence as shown. When the sequence obtained for intron 10 was aligned with the published cDNA sequence, it was discovered that the splice junctions had been incorrectly defined, so that the last 12 bases of exon 10 were in fact encoded by exon 11. Furthermore, when the entire intron was sequenced, rather than being greater than 8 kilobases (kb) in length as originally believed, it was found to be 456 bp. Using primers located in introns 16 and 18 (forward and reverse primers, respectively), an amplicon was generated from the second clone, RPCI-5.1150_E_8 and then sequenced to determine the sequence of the 3' end of intron 7. Boxes show each exon and its length in base pairs (intron length not drawn to scale). Primers used to amplify each exon are shown over and under the exonic structure (arrowheads). Exon-intron boundaries of exons 9, 10, 11 and 17 are shown in the upper part of the diagram (uppercase= exon, lowercase=intron), and he region covered by the two PAC clones is illustrated by the two lines at the bottom of the figure. The approximate location of the sequence polymorphisms, discovered in the families with severe hyperglycerolemia, are indicated by the arrows. The polymorphic base and surrounding sequence appear beneath the arrows (SEQ ID NOS: 20–23).

Identification of a Missense Mutation in Exon 10 Within Families With Severe Hyperglycerolemia:

All 20 GK exons, and their corresponding inton-exon boundaries, were screened for mutations. Two polymorphisms were discovered within the introns, and two within the exons (FIG. 2). Neither of the intronic polymorphisms is expected to lead to a functional difference. Based on the predicted amino acid sequence for this gene, the polymorphism in exon 3 is silent, whereas the polymorphism in exon 10 results in a missence mutation. Specifically, this latter nucleotide change results in a transition of an adenine (A) to a guanine (G), and this mutation (N288D) leads to the substitution of a small polar asparagine for a negatively charged aspartic acid (FIG. 3). Screening of the remaining family members demonstrated that this mutation was restricted to the 18 affected males and 14 obligate female carriers. This was not true of the other three polymorphisms since they were found in normoglycerolemic controls at frequencies greater than 10%. It is important to note that asparagine 288 is extremely well conserved in many different species, including *H. influenzae, M. pneumonia, E. coli,* yeast, and mice, as well as man (FIG. 3) (Pettigrew et al., *Arch Biochem Biophys* 349(2):236–245 (1998); Pettigrew et al., *J. Biol Chem* 263(1):135–139 (1988); Nevoigt et al., *FEMS Microbiol Rev*, 21(3):231–241 (1997)).

Phenotypic Expression of the N288D Mutation and Association of Fasting Glycerol Concentration With Impaired Glucose Tolerance and Abdominal Obesity:

The 18 affected males and the 14 obligate female carriers identified were matched for age (±5 years) and sex with unaffected relatives; their characteristics are presented in FIG. 8. Monitoring of plasma glycerol levels at 3–6 month intervals in N288D carriers demonstrated that the hyperglycerolemia was permanent, resulting in values greater than 2.5 mmol/L in men and 0.2 mmol/L in women. Carrying a GK gene mutation was also associated with a significantly higher BMI, waist circumference and total body fat, as well as with a higher mean of 2-hour glucose concentration following an OGTT.

Figure 4A:
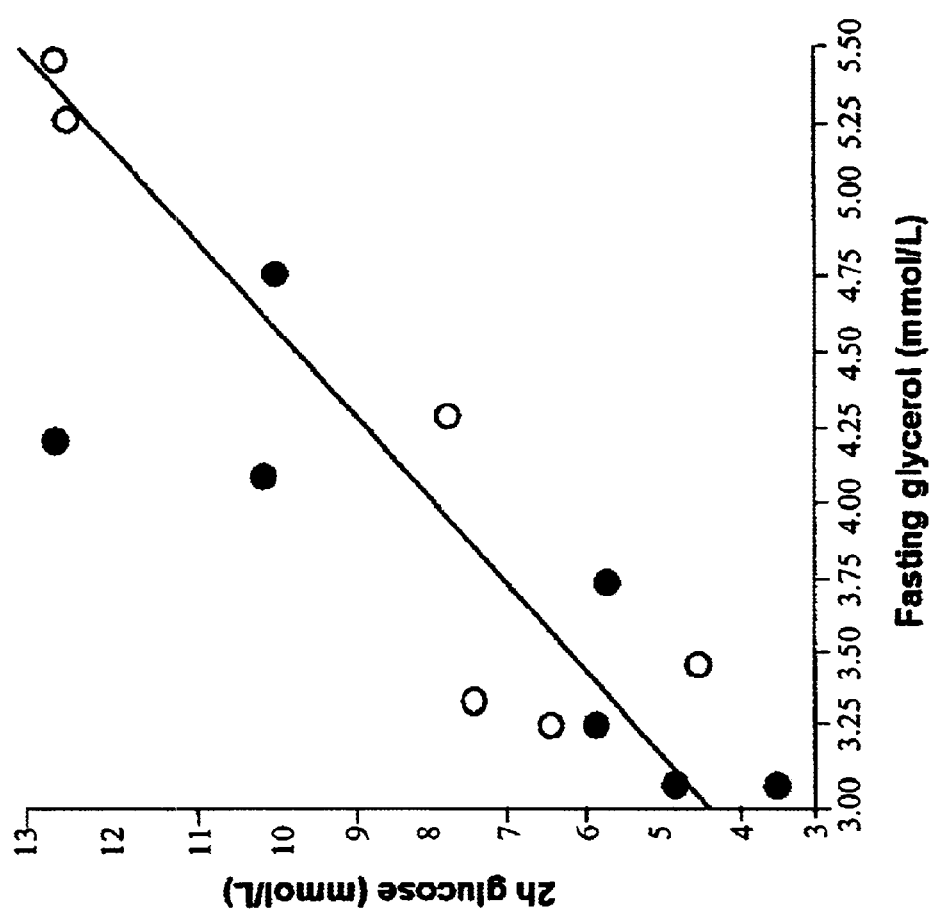
FIGS. 4A–4C are graphs of glycerol levels versus plasma glucose levels and waist girth, as well as mean plasma glycerol concentrations versus glucose tolerance.
Figure 4B:
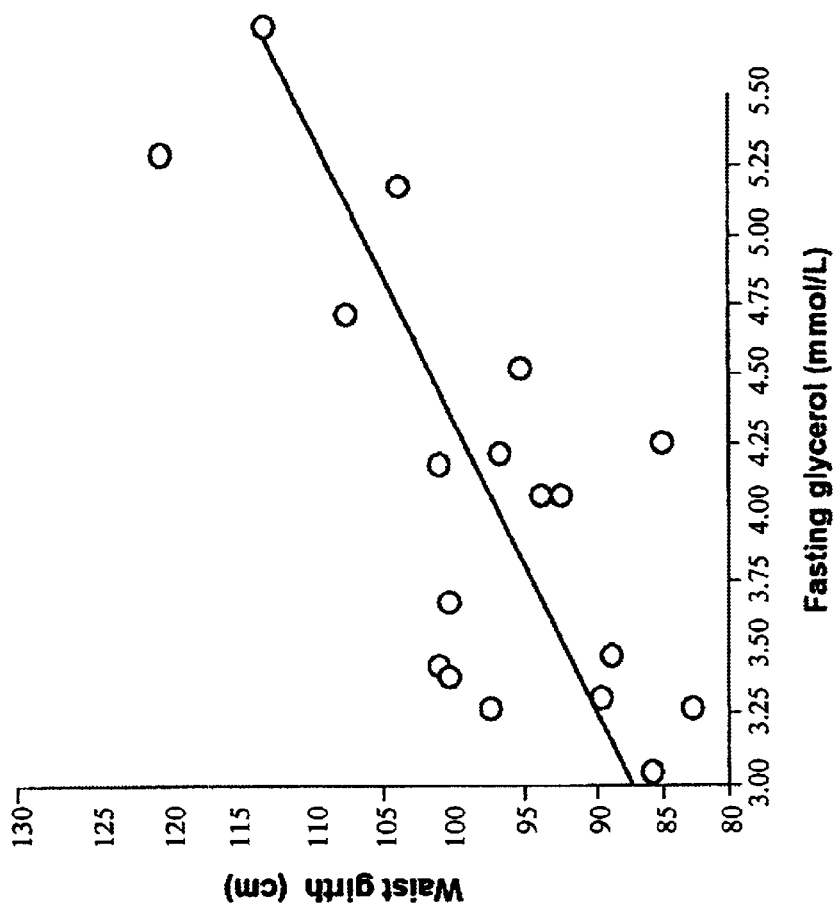

Further analysis of the association between glycerol and plasma glucose homeostasis as well as anthropometric indices of abdominal obesity in men carrying a N288D mutation showed that 12 of the 18 affected men met the criteria of either DM or IGT (FIG. 2). Among the six subjects with normal 2-hour glucose, four men showed elevated fasting insulinemia values (above 30 mU/L), which suggests that they were insulin-resistant. There was strong evidence that fluctuations in glycerolemia among carriers were important correlates of body fat accumulation and glucose concentrations. As illustrated in FIGS. 4A and 4B, plasma glycerol levels in affected males were related to variations in the waist circumference and 2-hour glucose levels following a 75 g oral absorption, such that 68.9% of the variance in 2-hour glucose values (p<0.0001) and 43% of the variance in waist circumference (p<0.001) were explained by the variance in glycerolemia among these subjects.

Figure 4C:
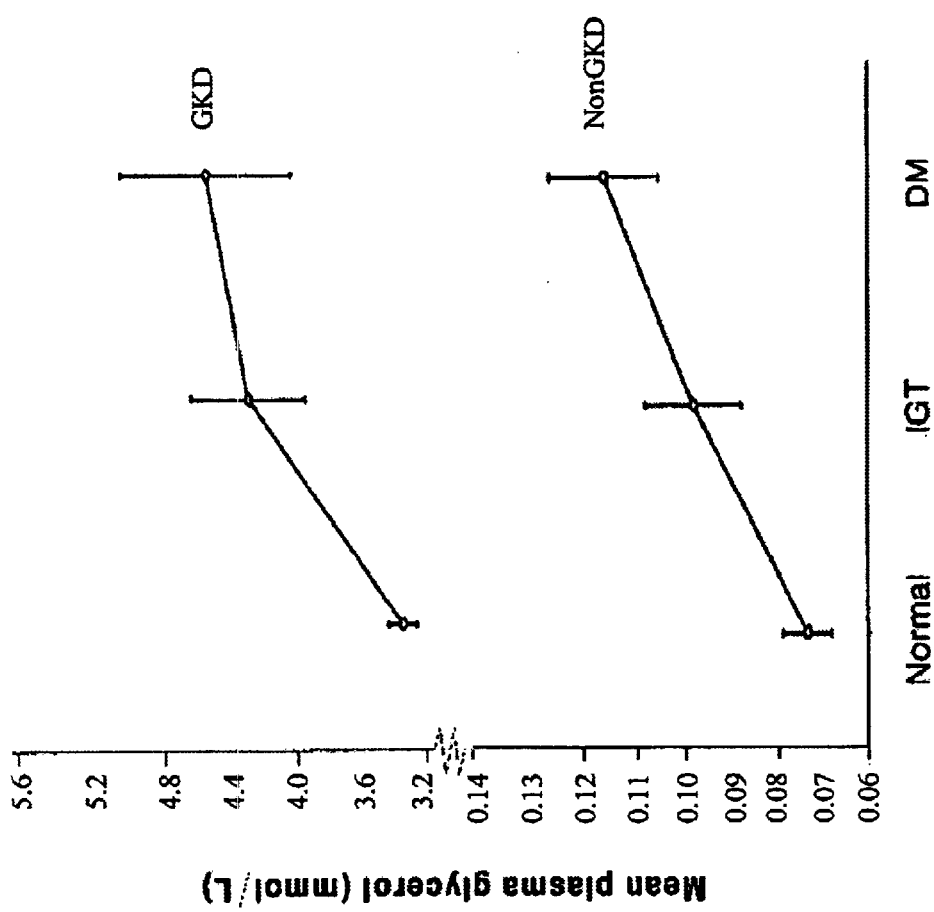

Plasma Glycerol Concentrations in the Original Cohort:

A similar trend was observed between the mean glycerol concentration and the degree of glucose intolerance in GK carriers as well as among subjects of the initial cohort with "normal" glycerol concentrations (FIG. 4C). As shown in FIG. 9, significant differences in fasting glycerol concentrations were also noted in the initial cohort in presence of impaired fasting glucose (values between 6.0–6.9 mmol/L), hyperinsulinemia, increased FFA concentrations, hypertriglyceridemia and obesity (defined as a BMI above 30 kg/m$^2$). Menopause, which characterized 59.6% of women, was associated with higher plasma glycerol values. Further stratification for the use of hormonal replacement therapy (HRT) showed an additional hormonal effect on the glycerolemia. For these reasons, appropriate adjustment for the effect of gender, menopause and HRT was performed in the different multivariate analyses.

Figure 5:
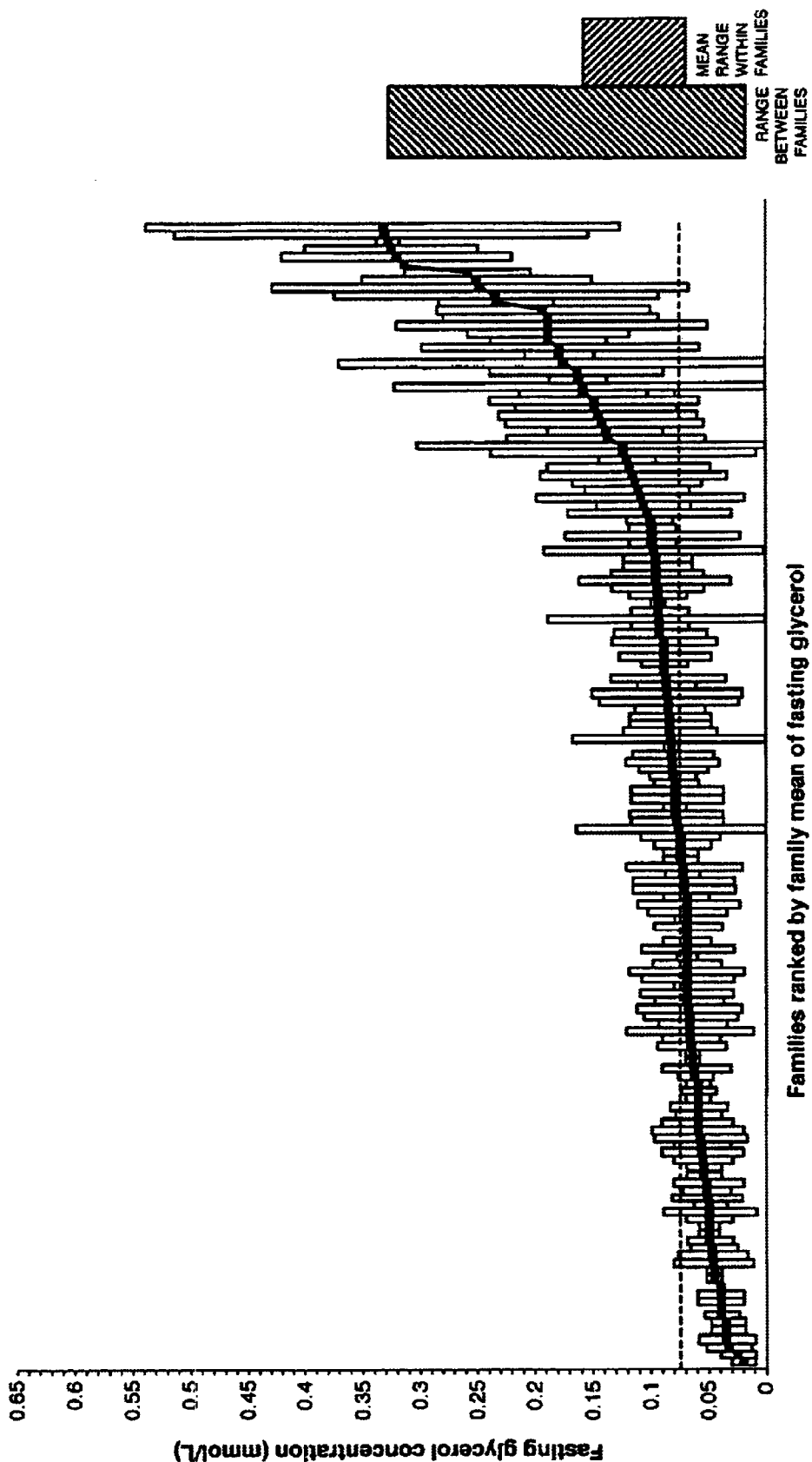
FIG. 5 shows the familial resemblance of plasma glycerol concentrations in the fasting state. Analyses were performed after having excluded families showing evidence of X-linked transmission of hyperglycerolemia due to a mutation in the GK gene. The age and sex adjusted fasting glycerol concentration was calculated as the residual from the regression model with covariates only, plus mean glycerolemia for the whole sample. The families are ranked according to plasma glycerol concentration in the fasting state. The range of mean glycerolemia between and within families are depicted by the hatched bars on the right. In the absence of GK gene mutation, a highly significant (p<0.0001) F ratio of 6.3 was observed, suggesting that there is over 6 times more variance between families than within them for plasma glycerol levels in the fasting state. The maximal heritability of glycerolemia in the fasting state has been estimated at 58% in the absence of severe hyperglycerolemia. The dotted line denotes median and geometric mean of plasma glycerol concentration (0.075 mmol/L) observed in the initial cohort of 1056 individuals (the probands).

Association of Fasting Glycerol Concentration With Impaired Glucose Tolerance in the Absence of Severe Hyperglycerolemia:

In multivariate analyses, after having excluded subjects with severe hyperglycerolemia and DM, a 1-standard deviation (SD) increase in log-glycerol was associated with a 2.5-fold increase in the risk of having 2-hour glucose between 7.8–11.0 mmol/L after a 75 g oral glucose challenge (FIG. 10). Furthermore, as illustrated in FIG. 5, the relative odds (OR) of having 2-hour glucose above 7.8 mmol/L after a 75 g oral glucose challenge was substantially increased among patients with glycerol concentration above the median (≧0.075 mmol/L) compared to those in the first decile (p<0.000), suggesting a threshold for glycerol concentrations above which there may be an increased risk of IGT.

Familial Resemblance of Plasma Glycerol Concentrations in the Absence of Severe Hyperglycerolemia:

Analyses of familial resemblance of plasma glycerol concentrations were performed on a sample of 652 individuals, probands and family members from 174 randomly-selected individuals from the original cohort, covering all deciles of fasting glycerol concentration. Overall, there was six times more variance in fasting plasma glycerol levels between than within families (FIG. 6). If it is assumed that the resemblance explained by belonging to the same pedigree is entirely defined by genetic factors, the maximal heritability of glycerolemia in the fasting state has been estimated at 58% in the absence of the GK gene N288D mutation.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of predicting impaired glucose tolerance in an individual, comprising the steps of:
   a) obtaining a nucleic acid sample from an individual;
   b) determining the nucleotide present at nucleotide position 29 of exon 10 of a glycerol kinase gene comprising SEQ ID NO: 5,
wherein presence of a guanine at said position is predictive of impaired glucose tolerance in the individual as compared with an individual having an adenosine at said position.

2. A method of predicting hyperglycerolemia in an individual, comprising the steps of:
   a) obtaining a nucleic acid sample from an individual;
   b) determining the nucleotide present at nucleotide position 29 of exon 10 of a glycerol kinase gene comprising SEQ ED NO: 5,
wherein presence of a guanine at said position is predictive of hyperglycerolemia in the individual as compared with an individual having an adenosine at said position.

3. A method of assisting in the prediction of cardiovascular disease in an individual, comprising the steps of:
   a) obtaining a nucleic acid sample from an individual;
   b) determining the nucleotide present at nucleotide position 29 of exon 10 of a glycerol kinase gene comprising SEQ ID NO: 5,
wherein presence of a guanine at said position is predictive of cardiovascular disease in the individual as compared with an individual having an adenosine at said position.

4. A method of assisting in the prediction of impaired glucose tolerance in an individual, comprising the steps of:
   a) obtaining a nucleic acid sample from an individual;
   b) determining the nucleotide present at nucleotide position 29 of exon 10 of a glycerol kinase gene comprising SEQ ID NO: 5,
wherein presence of guanine at said position is predictive of impaired glucose tolerance in the individual as compared with an individual having an adenosine at said position.

5. A method of assisting in the prediction of type 2 diabetes mellitus in an individual, comprising the steps of:
   a) obtaining a nucleic acid sample from an individual;
   b) determining the nucleotide present at nucleotide position 29 of exon 10 of a glycerol kinase gene comprising SEQ ID NO: 5,
wherein presence of a guanine at said position is predictive of Type 2 diabetes mellitus in the individual as compared with an individual having an adenosine at said position.

6. A method of assisting in the prediction of hyperglycerolemia in an individual, comprising the steps of:
   a) obtaining a nucleic acid sample from an individual;
   b) determining the nucleotide present at nucleotide position 29 of exon 10 of a glycerol kinase gene comprising SEQ ID NO: 5,
wherein presence of a guanine at said position is predictive of hyperglycerolemia in the individual as compared with an individual having an adenosine at said position.

7. A method of assisting in the prediction of diabetes mellitus in an individual, comprising the steps of:
   a) obtaining a nucleic acid sample from an individual;
   b) determining the nucleotide present at nucleotide position 29 of exon 10 of a glycerol kinase gene comprising SEQ ID NO: 5,
wherein presence of a guanine at said position is predictive of diabetes mellitus in the individual as compared with an individual having an adenosine at said position.

* * * * *

UNITED STATES PATENT AND TRADEMARK OFFICE
CERTIFICATE OF CORRECTION

PATENT NO. : 6,743,579 B1
DATED : June 1, 2004
INVENTOR(S) : Gaudet et al.

It is certified that error appears in the above-identified patent and that said Letters Patent is hereby corrected as shown below:

Column 41,
Line 36, "SEQ ED" should read -- SEQ ID --;
Line 21, -- a -- should be added after "presence of";

Column 42,
Line 31, "Type" should read -- type --.

Signed and Sealed this

Twenty-first Day of December, 2004

JON W. DUDAS
*Director of the United States Patent and Trademark Office*